(12) United States Patent
Tahir

(10) Patent No.: US 12,269,014 B1
(45) Date of Patent: Apr. 8, 2025

(54) $V_2C@V_2O_5/TiO_2$ COMPOSITE PHOTOCATALYST, PREPARATION METHOD, AND APPLICATION THEREOF

(71) Applicant: United Arab Emirates University, Al Ain (AE)

(72) Inventor: Muhammad Tahir, Al Ain (AE)

(73) Assignee: UNITED ARAB EMIRATES UNIVERSITY, Al-Ain (AE)

( * ) Notice: Subject to any disclaimer, the term of this patent is extended or adjusted under 35 U.S.C. 154(b) by 0 days.

(21) Appl. No.: 18/663,532

(22) Filed: May 14, 2024

(51) Int. Cl.
| | |
|---|---|
| B01J 23/22 | (2006.01) |
| B01J 35/39 | (2024.01) |
| B01J 37/00 | (2006.01) |
| B01J 37/04 | (2006.01) |
| B01J 37/08 | (2006.01) |
| C01B 32/40 | (2017.01) |
| C07C 5/32 | (2006.01) |

(52) U.S. Cl.
CPC ............ *B01J 23/22* (2013.01); *B01J 35/39* (2024.01); *B01J 37/0036* (2013.01); *B01J 37/0045* (2013.01); *B01J 37/04* (2013.01); *B01J 37/08* (2013.01); *C01B 32/40* (2017.08); *C07C 5/322* (2013.01); *C07C 2523/22* (2013.01)

(58) Field of Classification Search
None
See application file for complete search history.

(56) References Cited

PUBLICATIONS

Zaka, V2C MXene-TiO2 nanocomposite as an efficient electrode material for oxygen evolution reaction, vol. 48, issue 89, pp. 34599-34609 (Year: 2023).*
Cai, electric-field harmony in V2C/V2O5 heterointerfaces toward high performance aqueous Zn ion batteries, energy storage materials, vol. 60, 102835 (Year: 2023).*

* cited by examiner

*Primary Examiner* — Stefanie J Cohen
(74) *Attorney, Agent, or Firm* — MH2 Technology Law Group, LLP

(57) ABSTRACT

A composite photocatalyst, comprising $V_2C@V_2O_5/TiO_2$, is disclosed herein. Additionally, a process for producing this composite, particularly $V_2C@V_2O_5/TiO_2$, involves the steps of preparing $V_2C@V_2O_5/TiO_2$ composite; grinding the $V_2C@V_2O_5/TiO_2$ composite; and calcining the ground product to obtain the composite photocatalyst $V_2C@V_2O_5/TiO_2$. Furthermore, the disclosure encompasses utilizing the composite photocatalyst in a $CO_2$ reduction process, wherein the photocatalyst is irradiated in a photoreactor system.

11 Claims, 14 Drawing Sheets

$V_2C@V_2O_5/TiO_2$ COMPOSITE PHOTOCATALYST, PREPARATION METHOD, AND APPLICATION THEREOF

TECHNICAL FIELD

The present disclosure relates to a field of composite photocatalysts and preparation methods thereof. In particular the present disclosure relates to a $V_2C@V_2O_5/TiO_2$ composite photocatalyst and a preparation method and application thereof.

BACKGROUND

Carbon dioxide ($CO_2$), a prominent greenhouse gas, significantly contributes to climate change by trapping heat in the atmosphere, leading to global warming and associated environmental disruptions. Human activities, including the combustion of fossil fuels (coal and natural gas) for energy, industrial processes, deforestation, and certain agricultural practices, are the primary sources of $CO_2$ emissions. The conversion of $CO_2$ into valuable chemicals and fuels through photocatalytic processes offers a promising solution.

Current photocatalysts, while showing promise, are often limited by factors such as low efficiency, poor selectivity, and high recombination rates of photoinduced electron-hole pairs.

Traditional photocatalysts like titanium dioxide ($TiO_2$) suffer from large band gaps and limited light absorption, hindering their effectiveness in $CO_2$ conversion. Despite efforts to enhance their performance through composite structures and doping strategies, these materials fall short of achieving the desired level of efficiency and/or selectivity.

Recent studies have explored a range of materials and strategies to enhance photocatalytic $CO_2$ conversion. Semiconductor materials such as g-$C_3N_4$, $ZnIn_2S_4$, and $ZnFe_2O_4$ have shown potential in improving photocatalytic activity through heterojunction formation and band structure engineering. Additionally, MXenes, a class of two-dimensional nanomaterials, have also garnered attention for photocatalytic applications. MXenes, with the general formula $M_n+1X_n$, consist of early transition metals (M) and carbide, nitride, or carbonitride layers (X).

However, known catalysts suffer from drawbacks such as limited efficiency, reduced photostability, shorter catalytic activity, and considerable costs associated with their maintenance and replacement. Some may exhibit instability or deactivation over time, necessitating frequent regeneration or replacement, which adds complexity to their handling and increases overall operational costs. Additionally, certain catalysts may have narrow application ranges or limited versatility, further complicating their use and diminishing their effectiveness in different photocatalytic processes. Furthermore, the susceptibility of certain catalysts to side reactions or the production of undesired by-products can significantly impact the purity and yield of the desired chemicals or fuels, adding another layer of complexity to their application.

Therefore, there is a need to address the one or more limitations associated with existing catalysts used in the photocatalytic processes of $CO_2$ reduction.

SUMMARY

Accordingly, provided herein is a composite photocatalyst comprising $V_2C@V_2O_5/TiO_2$, wherein $V_2C$ is from about 5 wt. % to about 30 wt. %; $V_2O_5$ is from about 1% to about 10 wt. %; and $TiO_2$ is from about 60% to about 99 wt. %. This composite photocatalyst addresses one or more limitations associated with existing catalysts used in the photocatalytic processes of $CO_2$ reduction.

In another aspect, the present disclosure provides a process for preparing a composite comprising $V_2C@V_2O_5/TiO_2$. The process comprises the steps of: preparing a $V_2C/TiO_2$ composite; grinding the $V_2C/TiO_2$ composite; and calcining the ground product at about 400 to 700° C. for about 1 h to about 5 h to obtain the composite photocatalyst $V_2C@V_2O_5/TiO_2$.

In yet another aspect, the present disclosure provides a composite photocatalyst comprising $V_2C@V_2O_5/TiO_2$ prepared by the process of the preceding aspect.

The present disclosure further provides a process for $CO_2$ reduction. The process comprises contacting a feed comprising $CO_2$ and at least one sacrificial compound with a composite photocatalyst provided in the preceding aspect(s), in a photocatalytic system; and irradiating the photocatalyst with at least one irradiation source.

The present disclosure also provides a use of the composite photocatalyst provided in the preceding aspect(s), particularly for photocatalytic $CO_2$ reduction.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with the detailed description below, are incorporated in and form part of the specification, and serve to further illustrate the embodiments and explain various principles and advantages, in accordance with the present disclosure where:

Figure 9:
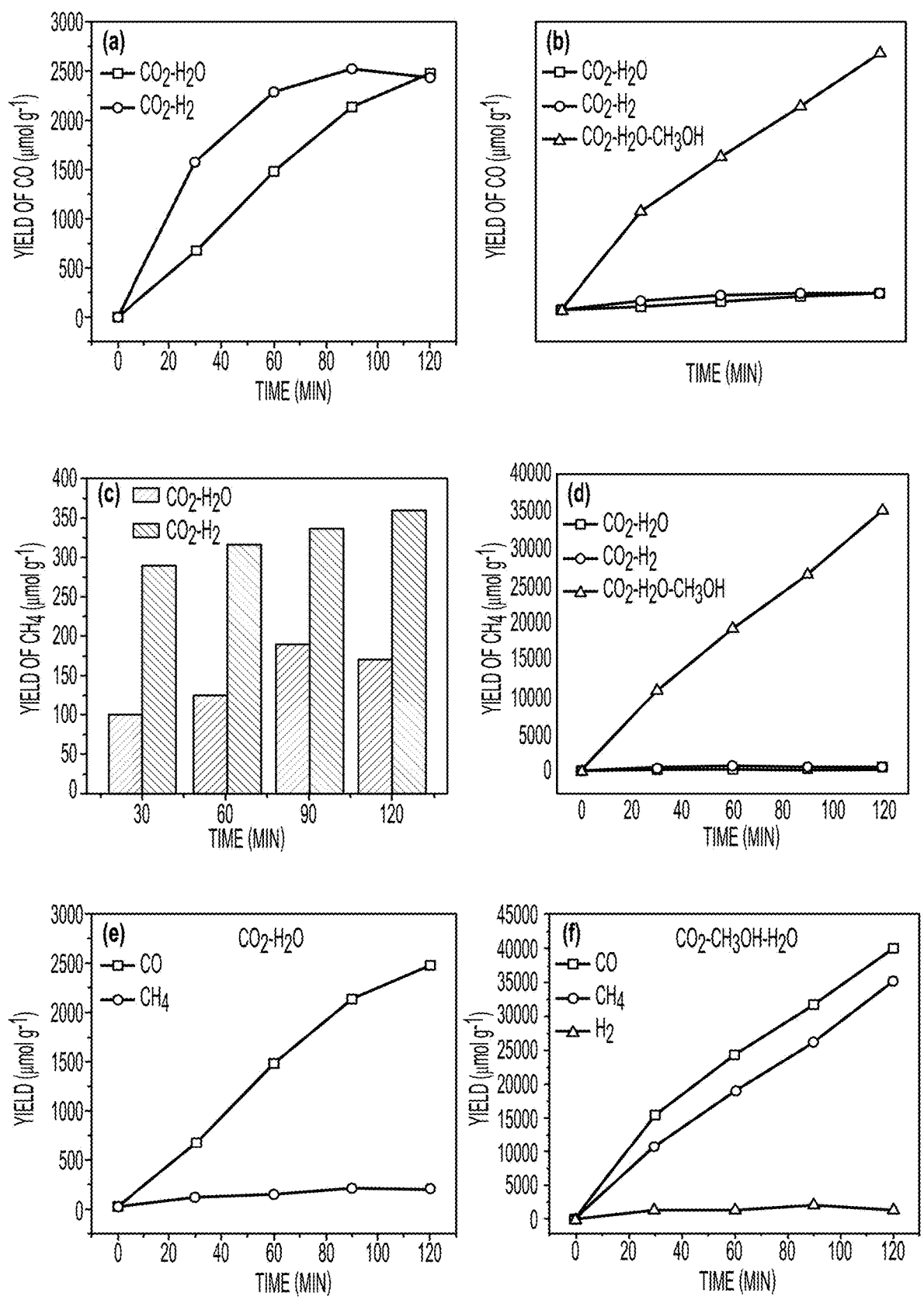

FIG. 9 shows performance of $V_2C@V_2O_5/TiO_2$ with different reforming reactions during $CO_2$ reduction reactions: (a) CO formation with $H_2O/H_2$ reducing agents, (b) CO formation with $CH_3OH/H_2O$ and $H_2$ reducing agents, (c) $CH_4$ formation with $H_2O/H_2$ reducing agents, (d) $CH_4$ formation with $CH_3OH/H_2O$ and $H_2$ reducing agents, (e) CO and $CH_4$ formation with $CO_2$—$H_2O$, (f) CO, $CH_4$ and $H_2$ formation with methanol sacrificial reagent.

Figure 10:
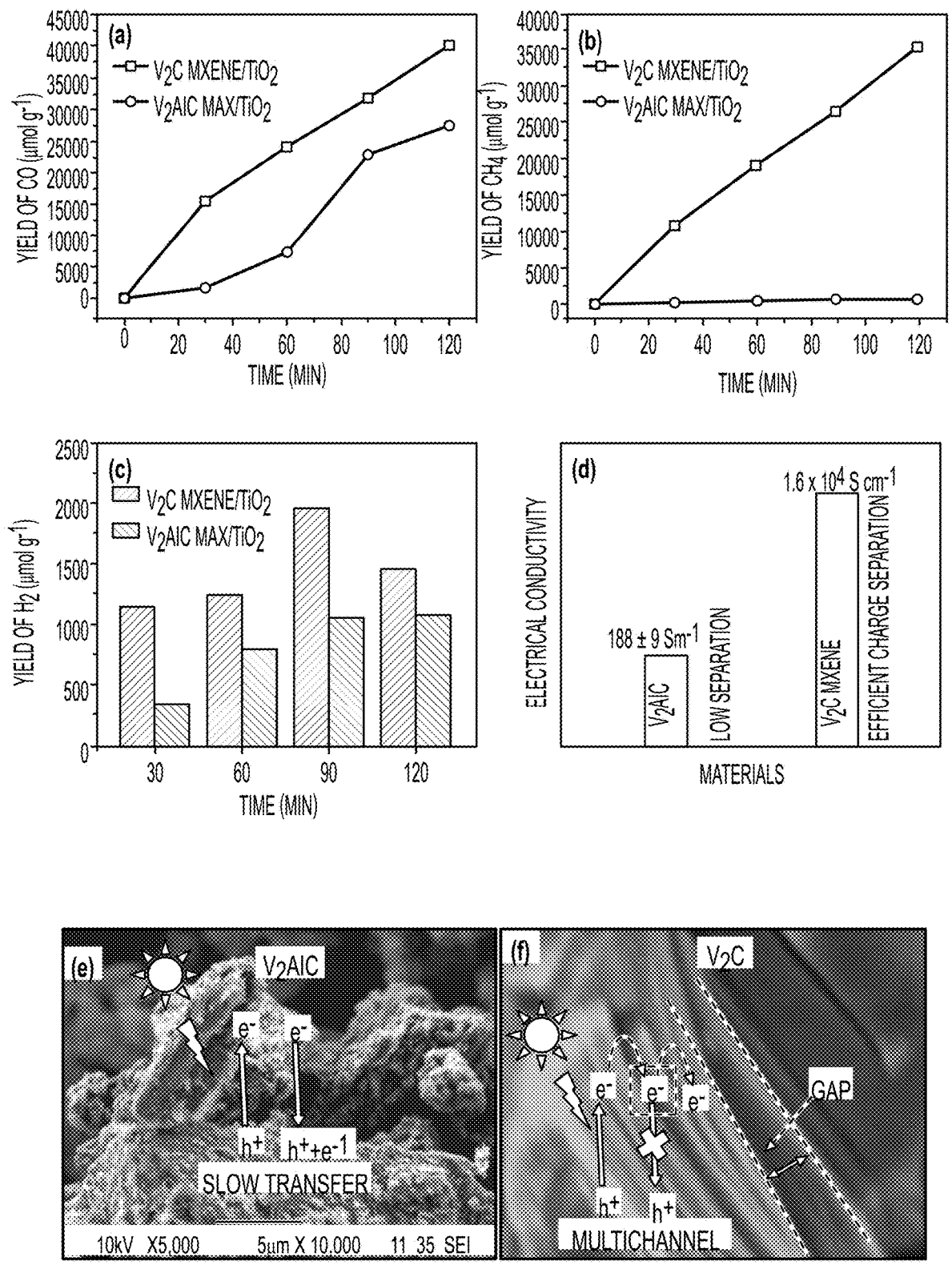

FIG. 10 shows (a) performance comparison of $V_2AlC$ MAX/$TiO_2$ and $V_2C$ MXene/$TiO_2$ composites for photocatalytic $CO_2$ reduction with methanol, (a) Co formation, (b) $CH_4$ formation, (c) $H_2$ formation, (d) comparison of electrical conductivity characteristics of $V_2AlC$ and $V_2C$ MXene, (e) charge separation mechanism over $V_2AlC$ MAX, (f) charge separation mechanism over $V_2C$ MXene.

Figure 11:
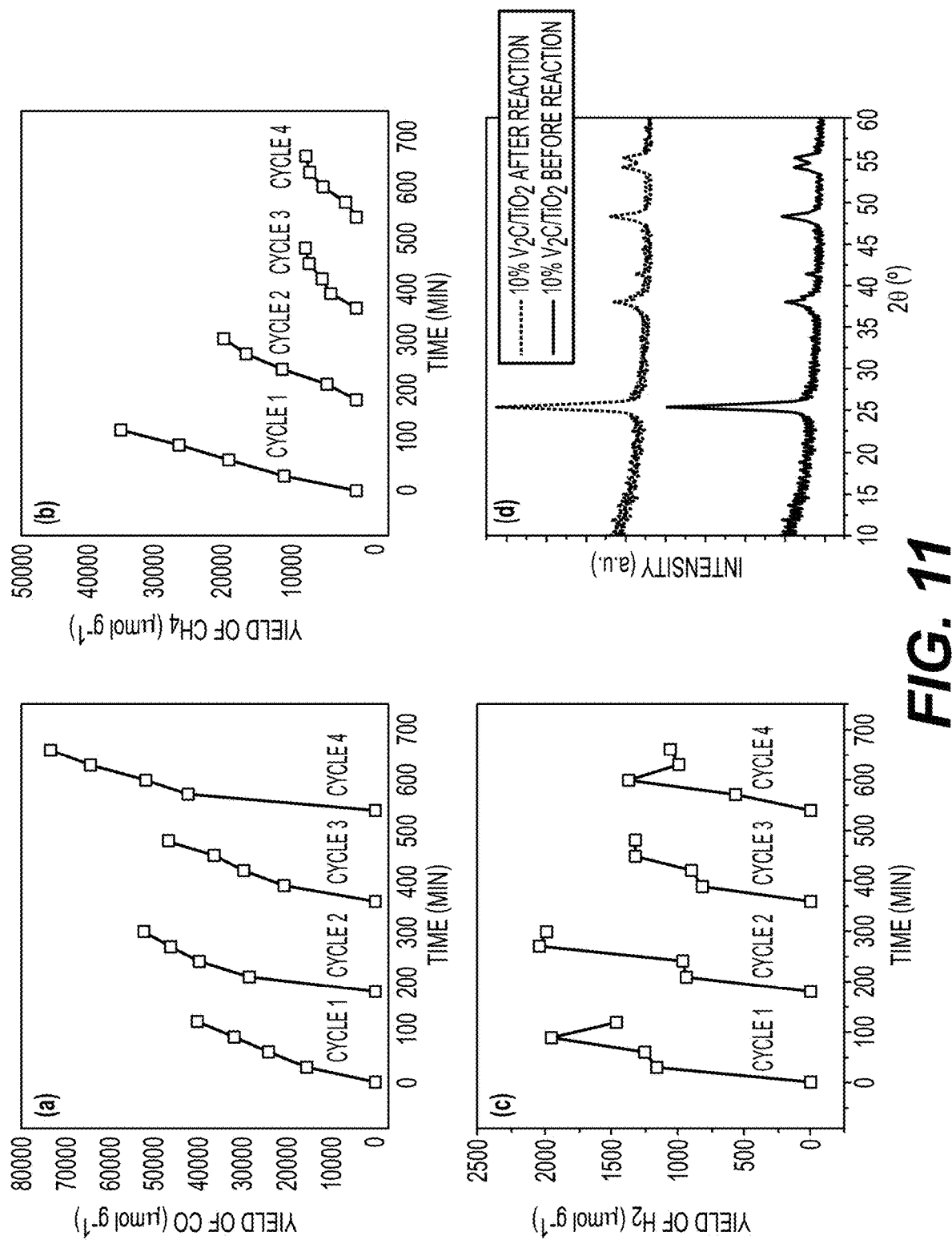

FIG. 11 shows cyclic stability assessment of $V_2C@V_2O_5/TiO_2$ composite for photocatalytic $CO_2$ reduction through bi-reforming of methanol for (a) CO yield, (b) $CH_4$ yield and (c) $H_2$ yield, (d) XRD analysis of fresh and spent catalyst of $V_2C@V_2O_5/TiO_2$ composite.

Figure 12:
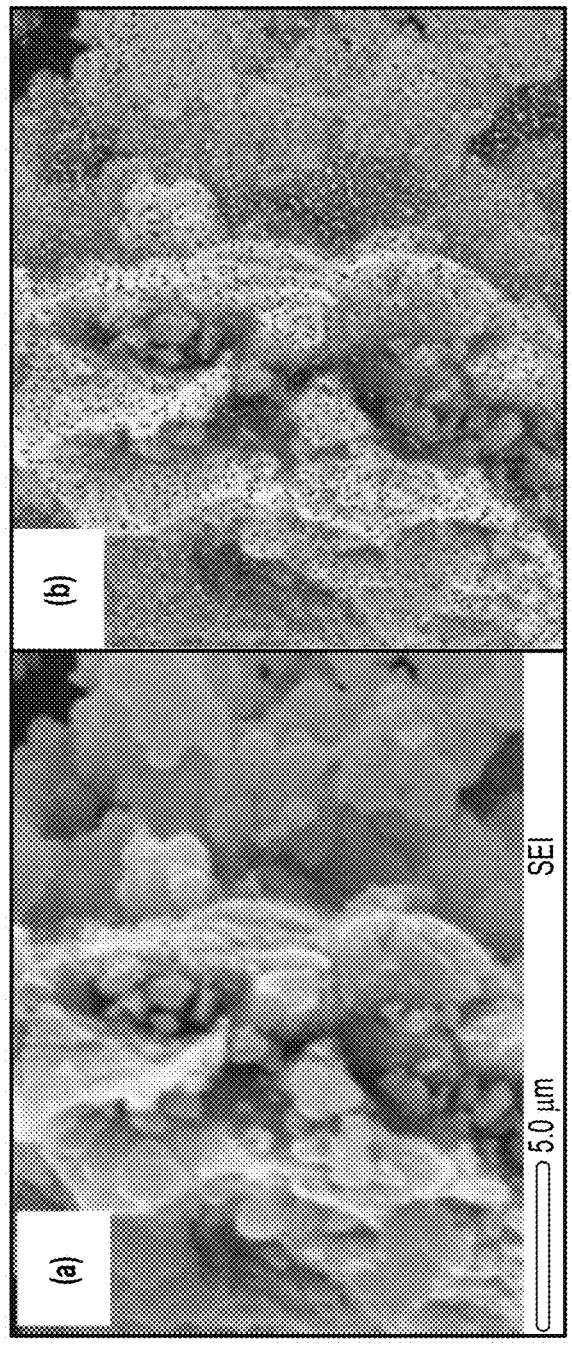
Figure 12:
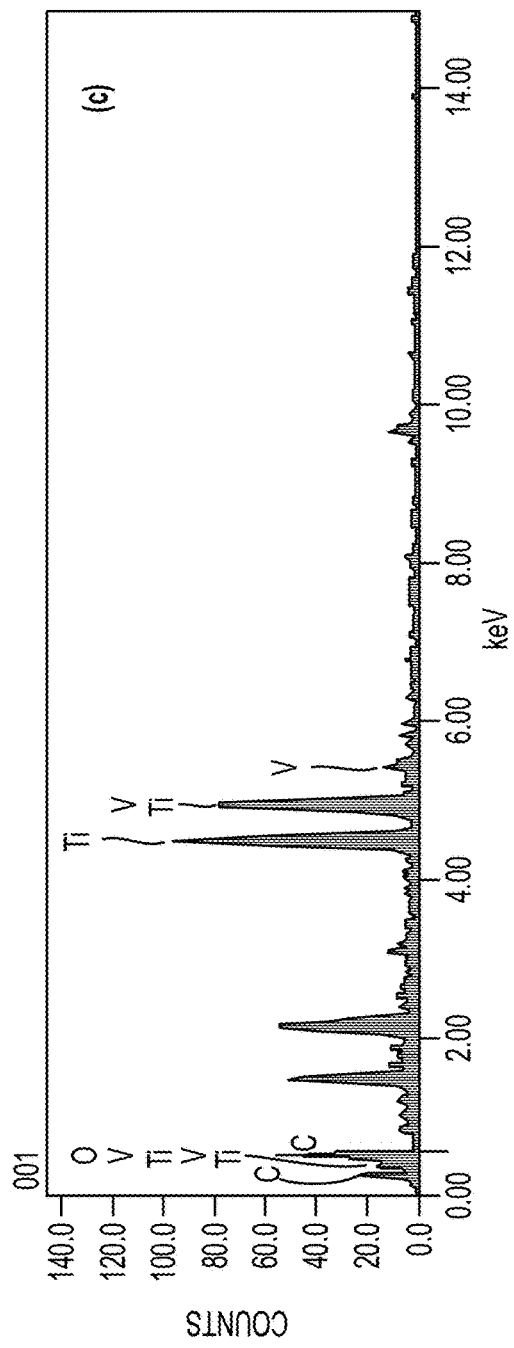

FIG. 12 shows (a) SEM image of spent $V_2C@V_2O_5/TiO_2$ composite, (b) EDS mapping analysis of $V_2C@V_2O_5/TiO_2$, (c) EDX spectra to confirm the presence of V, Ti, O and C.

Figure 13:
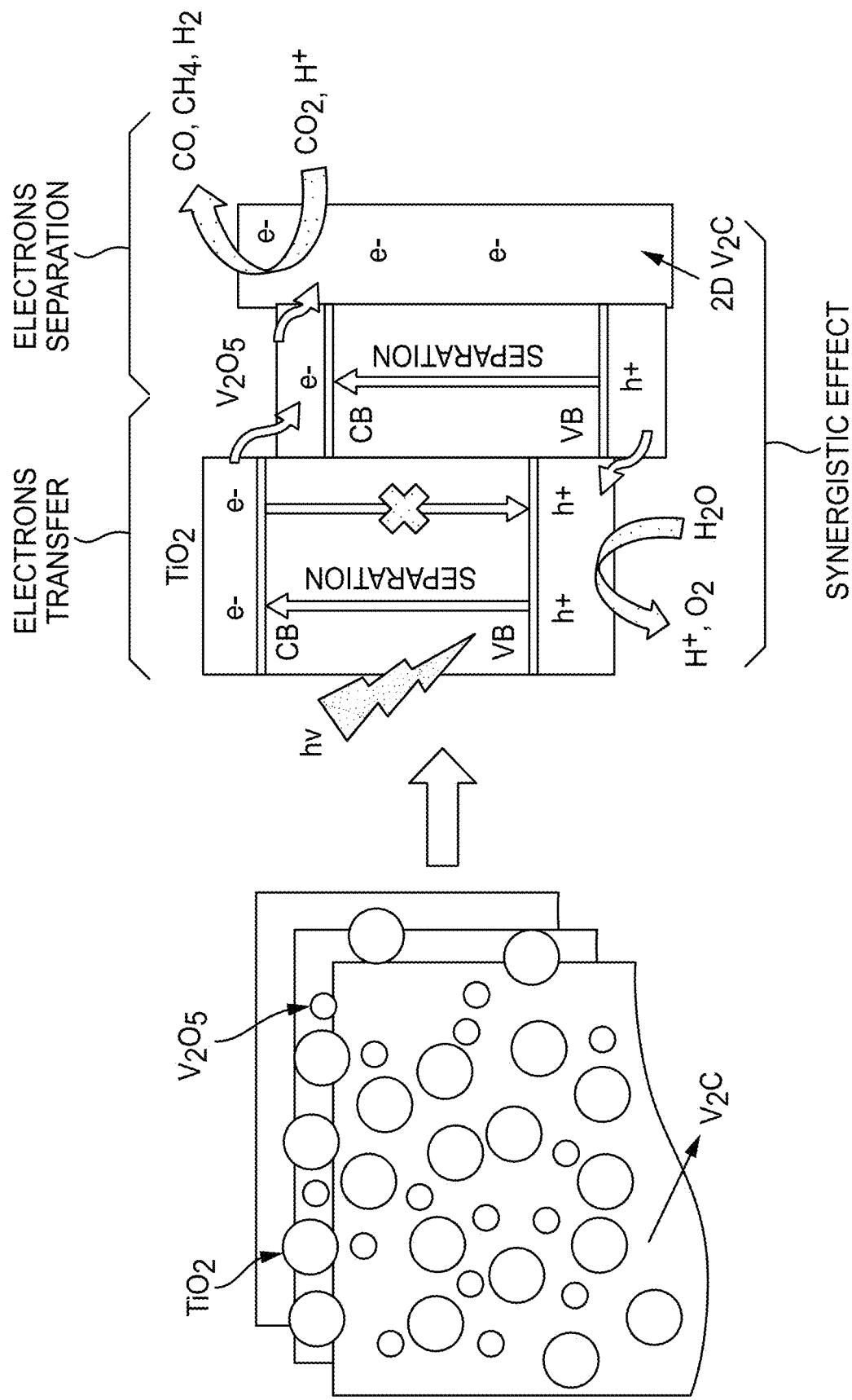

FIG. 13 shows the proposed mechanism for photocatalytic $CO_2$ reduction to CO, $CH_4$ and $H_2$ over $V_2C@V_2O_5/TiO_2$ composite.

DETAILED DESCRIPTION

The present disclosure is directed to a composite photocatalyst comprising $V_2C@V_2O_5/TiO_2$, preparation method, and application thereof. This composite photocatalyst addresses one or more limitations associated with existing catalysts used in the photocatalytic processes of $CO_2$ reduction.

In one embodiment of the present disclosure, a cost-effective and efficient composite photocatalyst is provided for the photocatalytic reduction of $CO_2$ to fuels and/or chemicals. In certain embodiments, the present disclosure leverages the unique properties of vanadium carbide ($V_2CT_x$) MXenes for enhancing the photocatalytic activity towards $CO_2$ reduction.

The present disclosure can be understood more readily by reference to the following description taken in connection with the accompanying Figures and Examples, all of which form a part of this disclosure.

At the very outset of the detailed description, it may be understood that the ensuing description only illustrates a particular form of this invention. However, such a particular form is only an exemplary embodiment, and without intending to imply any limitation on the scope of this invention. Accordingly, the description is to be understood as an exemplary embodiment and teaching of invention and not intended to be taken restrictively.

Before the present disclosure or methods of the present disclosure are described in greater detail, it is to be understood that the specific products, methods, processes, conditions or parameters, are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, "about" can mean within one or more standard deviations, or within ±30%, 25%, 20%, 15%, 10% or 5% of the stated value.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

All publications cited in this specification are herein incorporated by reference as if each individual publication was specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present products, composites or methods are not entitled to antedate such publication by virtue of prior invention.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or composites/scaffolds. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order which is logically possible.

The articles "a" and "an" are used herein to refer to one or to more than one (i.e., to at least one) of the grammatical object of the article. By way of example, "an element" means one element or more than one element.

As used herein, the term "comprises", "comprising", or "comprising of" is generally used in the sense of include, that is to say permitting the presence of one or more features or components. The term "comprises", "comprising", or "comprising of" when placed before the recitation of steps in a process or method means that the process or method encompasses one or more steps that are additional to those expressly recited, and that the additional one or more steps may be performed before, between, and/or after the recited steps. For example, a process or method comprising steps a, b, and c encompasses a process or method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the content clearly dictates otherwise. For example, a process or a method comprising steps a, b, and c encompasses, for example, a process or a method of performing steps in the order of steps a, c, and b, the order of steps c, b, and a, and the order of steps c, a, and b, etc.

Reference throughout this specification to "certain embodiments", "further embodiments", "some embodiments", "one embodiment", "an embodiment", "a non-limiting embodiment", "an exemplary embodiment", "some instances", or "further instances", means that a particular feature, structure or characteristic described in connection with the embodiment may be included in at least one embodiment of the present disclosure. Thus, the appearances of the "certain embodiments", "further embodiments", "some embodiments", "one embodiment", "an embodiment", "a non-limiting embodiment", "an exemplary embodiment", "some instances", or "further instances", in various places throughout this specification may not necessarily all refer to the same embodiment. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination.

As used herein, the terms 'include', 'have', 'comprise', 'contain' etc. or any form of said terms such as 'having', 'including', 'containing', 'comprising' or 'comprises' are inclusive and will be understood to imply the inclusion of a stated element, integer or step, or group of elements, integers or steps, but not the exclusion of any other element, integer or step, or group of elements, integers or steps.

The use of any and all examples, or exemplary language (e.g., "such as") provided with respect to certain embodiments herein is intended merely to better illustrate the disclosure and does not pose a limitation on the scope of the disclosure otherwise claimed.

As regards the embodiments characterized in this specification, it is intended that each embodiment be read independently as well as in combination with another embodiment. For instance, in case of an embodiment 1 reciting 3 alternatives A, B and C, an embodiment 2 reciting 3 alternatives D, E and F and an embodiment 3 reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

As used herein, the term "invention", "present invention", "disclosure" or "present disclosure" as used herein is a non-limiting term and is not intended to refer to any single embodiment of the particular invention but encompasses all possible embodiments as described in the specification.

The terms "process(es)" and "method(s)" are considered interchangeable within this disclosure.

In an embodiment, the present disclosure provides a composite photocatalyst comprising $V_2C@V_2O_5/TiO_2$; wherein $V_2C$ is from about 5 to about 30 wt. %; $V_2O_5$ is from about 1 to about 10 wt. %; and $TiO_2$ is from about 60 to about 99 wt. %.

In certain embodiments, $V_2C$ is about 5 to about 20 wt. %; $V_2O_5$ is from about 1 to about 5 wt. %; and $TiO_2$ is from about 80 to about 95 wt. %. In some embodiments, $V_2C$ is from about 10 to about 30 wt. %; $V_2O_5$ is from about 3 to about 10 wt. %; and $TiO_2$ is from about 60 to about 90 wt. %. In some instances, $V_2C$ is from about 5 to about 15 wt. %; $V_2O_5$ is from about 1 to about 3 wt. %; and $TiO_2$ is from about 70 to about 95 wt. %.

In certain embodiments, $V_2C$ may present in about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, or about 30 wt. %, In certain embodiments, $V_2O_5$ may present in about 1.0 wt. %, about 1.5 wt. %, about 2.0 wt. %, about 2.5 wt. %, about 3.0 wt. %, about 3.5 wt. %, about 4.0 wt. %, about 4.5 wt. %, about 5.0 wt. %, about 5.5 wt. %, about 6.0 wt. %, about 6.5 wt. %, about 7.0 wt. %, about 7.5 wt. %, about 8.0 wt. %, about 8.5 wt. %, about 9.0 wt. %, about 9.5 wt. %, or about 10.0 wt. %.

In certain embodiments, $TiO_2$ may present in about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, about 75 wt. %, about 76 wt. %, about 77 wt. %, about 78 wt. %, about 79 wt. %, about 80 wt. %, about 81 wt. %, about 82 wt. %, about 83 wt. %, about 84 wt. %, about 85 wt. %, about 86 wt. %, about 87 wt. %, about 88 wt. %, about 89 wt. %, about 90 wt. %, about 91 wt. %, about 92 wt. %, about 93 wt. %, about 94 wt. %, about 95 wt. %, about 96 wt. %, about 97 wt. %, about 98 wt. %, or about 99 wt. %.

In certain embodiments, the $V_2C@V_2O_5/TiO_2$ composite possesses superior characteristics, including elevated BET surface area, BJH surface area, increased pore volume, and enlarged mean pore radius when compared to $TiO_2$. In some embodiments, the $V_2C@V_2O_5/TiO_2$ composite showcases a synergistic enhancement, manifesting a collective improvement in BET surface area, pore volume, and mean pore radius relative to $TiO_2$. In some instances, the $V_2C@V_2O_5/TiO_2$ composite has a BET surface area of about 30 to 80 $m^2/g$, BJH surface area of about 40 to 120 $m^2/g$, pore volume of about 0.01 to 0.40 $cm^3/g$ and mean pore radius of about 3 to 30 nm. In further instances, the $V_2C@V_2O_5/TiO_2$ composite has a BET surface area of about 46.50 $m^2/g$, BJH surface area of about 77.18 $m^2/g$, pore volume of about 0.2018 $cm^3/g$ and mean pore radius of about 5.37 nm.

In certain embodiments, $TiO_2$ is distributed over the whole surface of $V_2C$ in the composite photocatalyst $V_2C@V_2O_5/TiO_2$.

In certain embodiments, all the elements of the composite (V, C, Ti and O) are evenly and/or uniformly distributed within the composite. In some embodiments, all the elements of the composite (V, C, Ti and O) are evenly and uniformly distributed within the composite.

In certain embodiments, the $V_2C@V_2O_5/TiO_2$ composite is a composite of $V_2C/TiO_2$ with in-situ grown $V_2O_5$; and it has a two-dimensional (2D)/zero-dimensional (0D)/zero-dimensional (0D) structure. Thus, in certain embodiments, the composite photocatalyst is 2D/0D/0D $V_2C@V_2O_5/TiO_2$ ternary composite.

In certain embodiments, 2D/0D/0D $V_2C@V_2O_5/TiO_2$ ternary composite is useful for achieving higher solar energy conversion efficiency, $CO_2$ conversion efficiency, and/or stability across multiple cycles, with CO, $CH_4$, and $H_2$ as the main products.

In certain embodiments, the composite photocatalyst comprising $V_2C@V_2O_5/TiO_2$ is a supported composite or an unsupported composite. In some embodiments, the composite photocatalyst comprising $V_2C@V_2O_5/TiO_2$ is a supported composite. The supported composite may be prepared by coating $V_2C@V_2O_5/TiO_2$ on a support. The $V_2C@V_2O_5/TiO_2$ can be coated on the support by any coating technique such as depositing, spin coating, spray coating, roll coating, curtain coating, casting and dipping. The support may be composed of various materials, such as ceramic ($SiO_2$, $Al_2O_3$, MgO and others), metal (steel, iron, cupper, and others), metal alloys Ni—Al, Al—Si, Fe—Al, Co—Ni—Cr, Ti—Ni—Cr and others, etc. In certain embodiments, the support is a monolithic support. A variety of shapes may be suitable for monolithic supports. These can include forms like honeycombs, foil, screens, plate, or a combination thereof. In certain embodiments, the support is a honeycomb support. When the support is a monolithic honeycomb support, the monolithic support's flow passages can vary in cross-sectional shape and size, including trapezoidal, rectangular, square, sinusoidal, hexagonal, elliptical, circular, among others. These monolithic substrates may accommodate up to about 800 or more flow channels (or "cells") per square inch of cross-section. In certain embodiments, supports may contain about 50 to about 700 cells per square inch ("CPSI"), about 100 CPSI to about 600 CPSI, about 200 CPSI to about 500 CPSI, or about 200 CPSI to about 400 CPSI. In some instances, monoliths used are with 200 CPSI. These cells can exhibit a variety of cross-sectional shapes, such as rectangular, square, circular, oval, triangular, hexagonal, or other polygonal forms. In certain embodiments, the support may be composed of a ceramic material. Non-limiting examples of ceramic materials include, $SiO_2$, $Al_2O_3$, MgO, and others. In certain embodiments, the support may be composed of a metal or metal alloys. Examples of metals include, but are not limited to, steel, iron, cupper, and others. Examples of metal alloys include, but are not limited to, Ni—Al, Al—Si, Fe—Al, Co—Ni—Cr, Ti—Ni—Cr and others.

In certain embodiments, the present disclosure provides $V_2C@V_2O_5/TiO_2$ composite catalyst and its application in photocatalytic processes, particularly in the reduction of carbon dioxide ($CO_2$). The composite catalyst harnesses the synergistic effect of $V_2C@V_2O_5$ to enhance the photocatalytic performance for these reactions.

The present disclosure thus also provides a process for preparing a composite photocatalyst comprising $V_2C@V_2O_5/TiO_2$. In certain embodiments, the process comprises preparing a 2D $V_2C$ MXenes layered structure and a $V_2C@V_2O_5/TiO_2$ composite.

In certain embodiments, the process for preparing the composite photocatalyst comprising $V_2C@V_2O_5/TiO_2$ comprises the steps of:
preparing a $V_2C/TiO_2$ composite;
grinding the $V_2C/TiO_2$ composite; and
calcining the ground product at about 400 to 700° C. for about 1 to 5 h to obtain the composite photocatalyst $V_2C@V_2O_5/TiO_2$.

In certain embodiments, the $V_2C@V_2O_5/TiO_2$ composite is prepared by single step sol-gel method.

In certain embodiments, the $V_2C@V_2O_5/TiO_2$ composite is prepared by the steps of:
a) mixing a titanium precursor and an alcohol solvent, and stirring to obtain a first solution;
b) mixing an acid with an alcohol solvent, and stirring to form a second solution;
c) mixing the second solution and the first solution, and stirring to obtain a third solution;
d) dispersing $V_2C$ in the alcohol solvent;
e) adding the dispersed $V_2C$ to the third solution to get a suspension, and stirring the suspension for a predetermined period; and
f) drying the suspension to obtain the $V_2C@V_2O_5/TiO_2$ composite.

Step a):

In certain embodiments of the process, in step a), the titanium precursor comprises a titanium alkoxide, a titanium oxide, a titanium halide (such as titanium chloride and the like), or a mixture thereof. In some embodiments, the titanium precursor comprises a titanium alkoxide. Examples of titanium alkoxide include, but are not limited to, titanium (IV) isopropoxide, titanium n-butoxide and titanium ethoxide, or a mixture thereof. In some embodiments, the titanium precursor comprises titanium (IV) isopropoxide.

In certain embodiments, the alcohol solvent comprises methanol, ethanol, or 2-propanol, or a mixture thereof. In some embodiments, the alcohol solvent comprises 2-propanol.

In certain embodiments, the ratio of the titanium source to the alcohol solvent is from about 1:1 to about 1:3. In some embodiments, the ratio of the titanium source to the alcohol solvent is about 1:1, about 1:1.5, about 1:2, about 1:2.5, or about 1:3.

In certain embodiments, the stirring is done at a temperature of about 10° C. to about 50° C. for about 15 min to about 60 min. In some embodiments, the stirring is done at room temperature for about 15 min to about 45 min, about 20 min to about 45 min, or about 25 min to about 45 min. In some embodiments, the stirring is done at room temperature for about 15 min, about 20 min, about 25 min, about 30 min, about 35 min, about 40 min, or about 45 min. In some instances, the stirring is done at room temperature for about 30 min.

Step b):

As described above, step b) comprises mixing an acid with an alcohol solvent, and stirring to form a second solution. In certain embodiments, the acid is an organic acid, or an inorganic acid. The acid comprises acetic acid, hydrochloric acid, nitric acid, or a mixture thereof. In certain embodiments, the acid comprises acetic acid.

In certain embodiments, the alcohol solvent is same as described above in step a). The ratio of the acid to the alcohol solvent is from about 0.5:1 to about 1:3. In some embodiments, the ratio of the acid to the alcohol solvent is about 0.5:1, about 0.6:1, about 0.7:1, about 0.8:1, or about 0.9:1, or about 1:1.

In certain embodiments, the stirring is done at a temperature of about 10° C. to about 50° C. for about 5 min to about 45 min. In some embodiments, the stirring is done at room temperature for about 5 min to about 40 min, about 5 min to about 35 min, about 5 min to about 30 min, for about 5 min, about 10 min, about 15 min, about 20 min, about 25 min, about 30 min, about 35 min, about 40 min, or about 45 min.

Step c):

Step c) comprises the mixing the second solution and the first solution, and stirring to obtain a third solution (titanium solution). In certain embodiments, the ratio of the first solution to the second solution is from about 1:0.5 to about 1:3. In some embodiments, the ratio of the first solution to the second solution is about 1:0.5, about 1:0.6, about 1:0.7, about 1:0.8, about 1:0.9, about 1:1, about 1:1.1, about 1:1.2, about 1:1.3, about 1:1.4, about 1:1.5, about 1:1.6, about 1:1.7, about 1:1.8, about 1:1.9, or about 1:2.

In certain embodiments, the stirring is done at a temperature of about 10° C. to about 50° C. for about 15 min to about 60 min. In some embodiments, the stirring is done at room temperature for about 15 min to about 45 min, about 20 min to about 45 min, or about 25 min to about 45 min. In some embodiments, the stirring is done at room temperature for about 15 min, about 20 min, about 25 min, about 30 min, about 35 min, about 40 min, or about 45 min. In some instances, the stirring is done at room temperature for about 30 min.

In some embodiments, the third solution (titanium sol) is obtained by hydrolyzing TTIP (Titanium (IV) isopropoxide) in acetic acid (1 M) using 10 mL of TTIP dissolved in 2-propanol.

Step d):

Step d) comprises dispersing $V_2C$ in the alcohol solvent. In certain embodiments, the dispersing is done at a temperature of about 10° C. to about 50° C. for about 15 min to about 60 min. In some embodiments, the dispersing is done at room temperature for about 15 min to about 60 min, about 15 min to about 45 min, about 20 min to about 45 min, or about 25 min to about 45 min. In some embodiments, the stirring is done at room temperature for about 10 min, about 15 min, about 20 min, about 25 min, about 30 min, about 35 min, about 40 min, or about 45 min. In some instances, the stirring is done at room temperature for about 10 min to about 30 min.

Step e)

Step e) comprises adding the dispersed $V_2C$ to the third solution to get a suspension, and stirring the suspension for a predetermined period. In certain embodiments, the ratio of $V_2C$ dispersed in the alcohol solvent to the third solution is from about 0.5:1 to about 1:3. In some embodiments, the ratio of $V_2C$ dispersed in the alcohol solvent to the third solution is about 0.5:1, about 0.6:1, about 0.7:1, about 0.8:1, about 0.9:1, about 1:1, about 1:1.1, about 1:1.2, about 1:1.3, about 1:1.4, about 1:1.5, about 1:1.6, about 1:1.7, about 1:1.8, about 1:1.9, about 1:2, about 1:2.1, about 1:2.2, about 1:2.3, about 1:2.4, about 1:2.5, about 1:2.6, about 1:2.7, about 1:2.8, about 1:2.9, or about 1:3.

In certain embodiments, the alcohol solvent is same as described above in step a). In some embodiments, about 5 to about 25 wt. % of $V_2C$ is dispersed in the alcohol solvent (e.g., 2-propanol). In some instances, about 5 to about 20 wt. %, or about 5 to about 15 wt. % of $V_2C$ is dispersed in the alcohol solvent. In further instances, about 5 wt. %, about 10 wt. %, or about 15 wt. % of $V_2C$ is dispersed in the alcohol solvent.

In certain embodiments, the addition of the dispersed $V_2C$ to the third solution results in a suspension. The suspension is stirred for a predetermined period. In certain embodiments, the suspension is stirred at a temperature of about 10° C. to about 50° C. for about 12 h to about 36 h. In some embodiments, the suspension is stirred at room temperature for about 20 h to 28 h. In some instances, the suspension is stirred at room temperature for about 24 h.

Step f):

Step f) comprises drying the suspension obtained in step e) to obtain a dried product. In certain embodiments, the drying is done at a temperature of about 80° C. to about 120° C. for about 4 h to about 32 h. Any drying technique, such as normal over drying, micro-oven drying, and the like, may be employed. In some embodiments, the suspension is oven-dried at about 80-120° C. overnight. In some instances, the suspension is oven-dried at about 100° C. for overnight to obtain the $V_2C@V_2O_5/TiO_2$ composite.

In certain embodiments of the process, the $V_2C@V_2O_5/TiO_2$ composite is subjected to griding. Any grinding technique known to those skilled in the art may be used. In some embodiments, the $V_2C@V_2O_5/TiO_2$ composite is ground to fine powder by ball mill and pestle and mortar. The ground product is then subjected to calcination to obtain the composite photocatalyst $V_2C@V_2O_5/TiO_2$. In certain embodiments, the calcination is done at about 500° C. for about 2 h.

In certain embodiments, $V_2C$ is prepared by etching of $V_2AlC$ MAX. in some embodiments. 2D $V_2C$ MXenes layered structures are prepared by hydrofluoric acid (HF) etching of $V_2AlC$ MAX.

In certain embodiments, $V_2C$ is prepared by the steps of:
a. mixing $V_2AlC$ with HF, and stirring to obtain a suspension;
b. washing the suspension with deionized water until a pH above 6.5 is achieved;
c. centrifuging the suspension to separate particulates from the liquid; and
d. drying the separated particulates to obtain $V_2C$.

Step g):

In certain embodiments, in step g), the ratio of $V_2AlC$ to HF is about 1:40 to about 1:150. In certain embodiments, the ratio of $V_2AlC$ to HF is about 1:100 to about 1:150. In some instances, the ratio of $V_2AlC$ to HF is about 1:110 to about 1:120, or about 1:115. In some embodiments, the stirring is done at room temperature for about 12 h to about 36 h. In some instances, the stirring is done at room temperature for about 24 h.

Step i):

Step i) comprises centrifuging the suspension obtained in step h) to separate particulates from the liquid. In certain embodiments, centrifugation is carried out at 6000-12000 rpm for 3 to 15 minutes at 20-40° C. Any centrifuge known to those skilled in the art can be used.

Step j):

Step j) comprises drying the particulates separated in step i) to obtain $V_2C$. In certain embodiments, the drying is done at a temperature of about 80° C. to about 120° C. for about 4 h to about 32 h. Any drying technique, such as normal over drying, micro-oven drying, and the like, may be employed. In some embodiments, the particulates are oven-dried at about 80-120° C. overnight. In some instances, the particulates are oven-dried at about 100° C. for overnight to obtain the $V_2C$.

In certain embodiments, the present disclosure provides a composite photocatalyst comprising $V_2C@V_2O_5/TiO_2$ prepared by the process of any of the preceding embodiments. In some embodiments, the composite photocatalyst prepared by the process of any of the preceding embodiments has the features described in the embodiments disclosed above, i.e., In certain embodiments, $V_2C@V_2O_5/TiO_2$ composite has a higher a higher BET surface area, BJH surface area, increased pore volume, and/or increased mean pore radius as compared to $TiO_2$. In some embodiments, the $V_2C@V_2O_5/TiO_2$ composite has a combination of a higher BET surface area, increased pore volume, and increased mean pore radius as compared to $TiO_2$. In certain embodiments, the $V_2C@V_2O_5/TiO_2$ composite possesses superior characteristics, including elevated BET surface area, BJH surface area, increased pore volume, and enlarged mean pore radius when compared to $TiO_2$. In some embodiments, the $V_2C@V_2O_5/TiO_2$ composite showcases a synergistic enhancement, manifesting a collective improvement in BET surface area, pore volume, and mean pore radius relative to $TiO_2$. In some instances, the $V_2C@V_2O_5/TiO_2$ composite has a BET surface area of 30=80 $m^2/g$, BJH surface area of 40-120 $m^2/g$, pore volume of 0.01-0.40 $cm^3/g$ and mean pore radius 3-30 nm. In further instances, the $V_2C@V_2O_5/TiO_2$ composite has a BET surface area of about 46.50 $m^2/g$, BJH surface area of about 77.18 $m^2/g$, pore volume of about 0.2018 $cm^3/g$ and mean pore radius of about 5.37 nm. In certain embodiments, $TiO_2$ is distributed over the whole surface of $V_2C$ in the composite photocatalyst comprising $V_2C@V_2O_5/TiO_2$. In some embodiments, all the elements of the composite (V, C, Ti and O) are evenly and uniformly distributed within the composite. In certain embodiments, the $V_2C@V_2O_5/TiO_2$ composite prepared by the process of the present disclosure is 2D/0D/OD $V_2C@V_2O_5/TiO_2$ ternary composite.

In certain embodiments, the composite photocatalyst comprising $V_2C@V_2O_5/TiO_2$ provided above or the composite photocatalyst prepared by the process of the present disclosure is useful for photocatalytic $CO_2$ reduction. Therefore, the present disclosure further provides a process for $CO_2$ reduction.

In certain embodiments, the present disclosure provides a process for $CO_2$ reduction, comprising:
  contacting a feed comprising $CO_2$ and at least one sacrificial compound with a composite photocatalyst comprising $V_2C@V_2O_5/TiO_2$ in a photocatalytic system; and
  irradiating the photocatalyst with at least one irradiation source.

In certain embodiments, the irradiation source can be UV visible light or infrared with a wavelength range of about 200 to 1000 nm. The UV range is from about 200 to 400 nm, the visible range is about 400 to 700 nm, and the infrared range is from about 700 to 1000 nm. The light intensity can be varied from about 10 $mW/cm^2$ to about 500 $mW/cm^2$ and it depends on the type of lamps used. Different types of lamps such as halogen, xenon, and mercury lamps with their different powers such as 10 W to 1000 W can be used to achieve above parameters.

In certain embodiments the process for $CO_2$ reduction is carried at a temperature of about 10° C. to about 100° C. and a pressure of about 1 to 10 bars. In some embodiments, the process is carried out at room temperature and atmospheric pressure. In some embodiments, the process for $CO_2$ reduction is carried for a time period of about 1 to 20 h.

In certain embodiments, the sacrificial compound comprises water, hydrogen ($H_2$), methane, methanol, ethanol, acetic acid, propanol, glycerol, TEOA, or a mixture thereof.

In some embodiments, the sacrificial compound comprises water. In some embodiments, the sacrificial compound comprises $H_2$. In some instances, the sacrificial compound comprises $H_2$-water mixture, or methanol-water mixture.

In certain embodiments, the photocatalytic system comprises a main reactor chamber, one or more cooling fans integrated with an irradiation light source, one or more mass flow controllers (MFC), and an online products analysis system.

According to the present disclosure, any light or irradiation source emitting wavelengths absorbable by the photocatalyst can be utilized for activation. These sources may include natural sources like sunlight or artificial sources such as lasers, Hg lamps, incandescent lamps, fluorescent tubes, plasma, or Light-Emitting Diodes (LEDs). In some embodiments, the irradiation source is a Hg lamp. In some embodiments, a 200 W Hg lamp having a light intensity of about 100 $mW/cm^2$ is used in the process.

In certain embodiments, the irradiation source is positioned external to the reactor, and their interaction occurs through an optical interface. This interface, which facilitates the diffusion of photons absorbable by the photocatalyst into the reactor, can be constructed from materials such as quartz, glass, or any other suitable material. In certain embodiments, the optical interface is a quartz glass window. In certain embodiments, the irradiation source located above the optical interface.

In certain embodiments, a water saturator is integrated into the reactor system to facilitate the transportation of moisture, or water-containing mixtures such as $H_2$-water mixture, methanol-water mixture, and the like along with $CO_2$. This integration ensures a controlled and efficient delivery of these compounds into the reactor environment. The water saturator operates by saturating the carrier gas, typically $CO_2$, with water vapor. By passing the $CO_2$ through the water saturator, moisture or the water-containing mixture becomes effectively carried along with the $CO_2$ stream into the reactor. This ensures a consistent and controlled supply of the desired compounds, essential for the successful execution of various photocatalytic processes within the reactor system.

In certain embodiments, the feed enters the reactor at the top and flows over the catalyst surface before exiting at the bottom. The bottom surface of the reactor chamber, where a uniformly distributed powder photocatalyst is present, serves as the primary area for interaction among the catalyst, reactants, and light source. Before commencing the experiments, a feed or feed mixture (e.g., $CO_2$ and $H_2O$) is continuously passed through the reactor for a predetermined time to saturate the catalyst surface.

Accordingly, in certain embodiments, the process for $CO_2$ reduction comprises:
  a) providing a photocatalytic system comprising a main reactor chamber, one or more cooling fans integrated with an irradiation light source, one or more mass flow controllers (MFC), and an online products analysis system;
  b) utilizing an irradiation source positioned above an optical interface which allows light/irradiation passage through the reactor system;
  c) integrating a water saturator with the reactor system for carrying the at least one sacrificial compound with $CO_2$;

d) introducing the feed at the top of the reactor and allowing it to flow over the composite photocatalyst surface before exiting at the bottom surface; wherein the composite photocatalyst comprises $V_2C@V_2O_5/TiO_2$; and e) passing the feed through the reactor before starting the experiments to saturate the catalyst surface;

In certain embodiments, in step e) of the process for $CO_2$ reduction, the feed is passed through the reactor for about 5 minutes to about 120 minutes before starting the experiments to saturate the catalyst surface.

In certain embodiments, the process is carried out in in liquid phase and/or in the gas phase. In some embodiments, the process is carried out in a gas-phase photocatalytic system.

In certain embodiments of the process for $CO_2$ reduction, $V_2C@V_2O_5/TiO_2$ is in powdered form.

In certain embodiments, the process produces CO and $CH_4$ through the photocatalytic reduction of $CO_2$ with water vapor in a gas-phase photocatalytic system. The addition of $V_2C$ to construct $V_2C/TiO_2$ composite enhances the photocatalytic activity, leading to increased CO production. In some embodiments, the highest CO yield is achieved with 10% $V_2C@V_2O_5/TiO_2$ composite, showing significant improvement over pure $V_2C$ and pure $TiO_2$ samples.

In certain embodiments, the process selectively or majorly produces CO when $CO_2$ reduction is carried out with water. In some embodiments, when $CO_2$ is reduced with a methanol-water mixture, both CO and $CH_4$ are produced in significant amounts.

In certain embodiments, when methanol is used as a hole scavenger, it enhances the conversion of $CO_2$ into CO over the $V_2C@V_2O_5/TiO_2$ composite. Methanol-water mixture exhibits superior performance compared to water and $H_2$, significantly increasing CO yield. The process involves increased proton and electron production during photocatalysis, facilitating $CO_2$ reduction to form CO.

In certain embodiments, the process yields $CH_4$ during photocatalytic $CO_2$ reduction with $H_2O$ and $H_2$. However, higher yields are achieved when employing methanol as the sacrificial reagent. Notably, the addition of a methanol-water mixture significantly enhances $CH_4$ generation compared to using water or $H_2$ alone.

In certain embodiments, the process for $CO_2$ reduction with $V_2C@V_2O_5/TiO_2$ composite simultaneously produces CO, $CH_4$, and $H_2$ during the methanol-driven reforming. This demonstrates the efficacy of the process in promoting multiple reaction pathways and facilitating the formation of diverse carbon-based products.

In certain embodiments, 2D/0D/OD $V_2C@V_2O_5/TiO_2$ ternary composite is useful for achieving higher solar energy conversion efficiency, $CO_2$ conversion efficiency, and stability across multiple cycles, with CO, $CH_4$, and $H_2$ as the main products.

In certain embodiments of the process, the $V_2C@V_2O_5/TiO_2$ composite continuously produces CO without deactivating, even after multiple cycles, such as four or more cycles.

The present disclosure is further described with reference to the following examples, which are only illustrative in nature and should not be construed to limit the scope of the present disclosure in any manner.

EXAMPLES

Experimental

Example 1: Synthesis of $V_2CT_x$ MXene

Vanadium aluminium carbide ($V_2AlC>98\%$, supplied by Famous Chem China) underwent wet chemical etching to yield 2D structured vanadium carbide ($V_2CT_x$) MXenes. In a Teflon-lined reactor, 1 g of $V_2AlC$ MAX was combined with 40 mL of 49% hydrogen fluoride (HF). The mixture was stirred for 24 hours at room temperature. Subsequently, the suspension underwent multiple rinses with deionized water until reaching a pH above 6.5. The particulates were separated from the liquid using a centrifuge. The resulting product, $V_2C$ MXene, was then dried in an oven overnight at 100° C.

Example 2: Synthesis of $V_2CT_x/TiO_2$ Binary Composite

The synthesis of the $V_2C@V_2O_5/TiO_2$ composite via the sol-gel process involved the utilization of titanium tetraisopropoxide (TTIP) as the precursor. By employing a defined process, the titanium sol was created through the hydrolysis of TTIP in acetic acid (1M), using 10 mL of TTIP dissolved in 2-propanol. Following a stirring period of 4 hours, a precise amount of $V_2C$, dispersed in 2propanol (10 mL), was added to the titanium solution. Subsequently, the resulting suspension underwent 24 hours of stirring before being subjected to overnight oven drying at 100° C.

Figure 1:
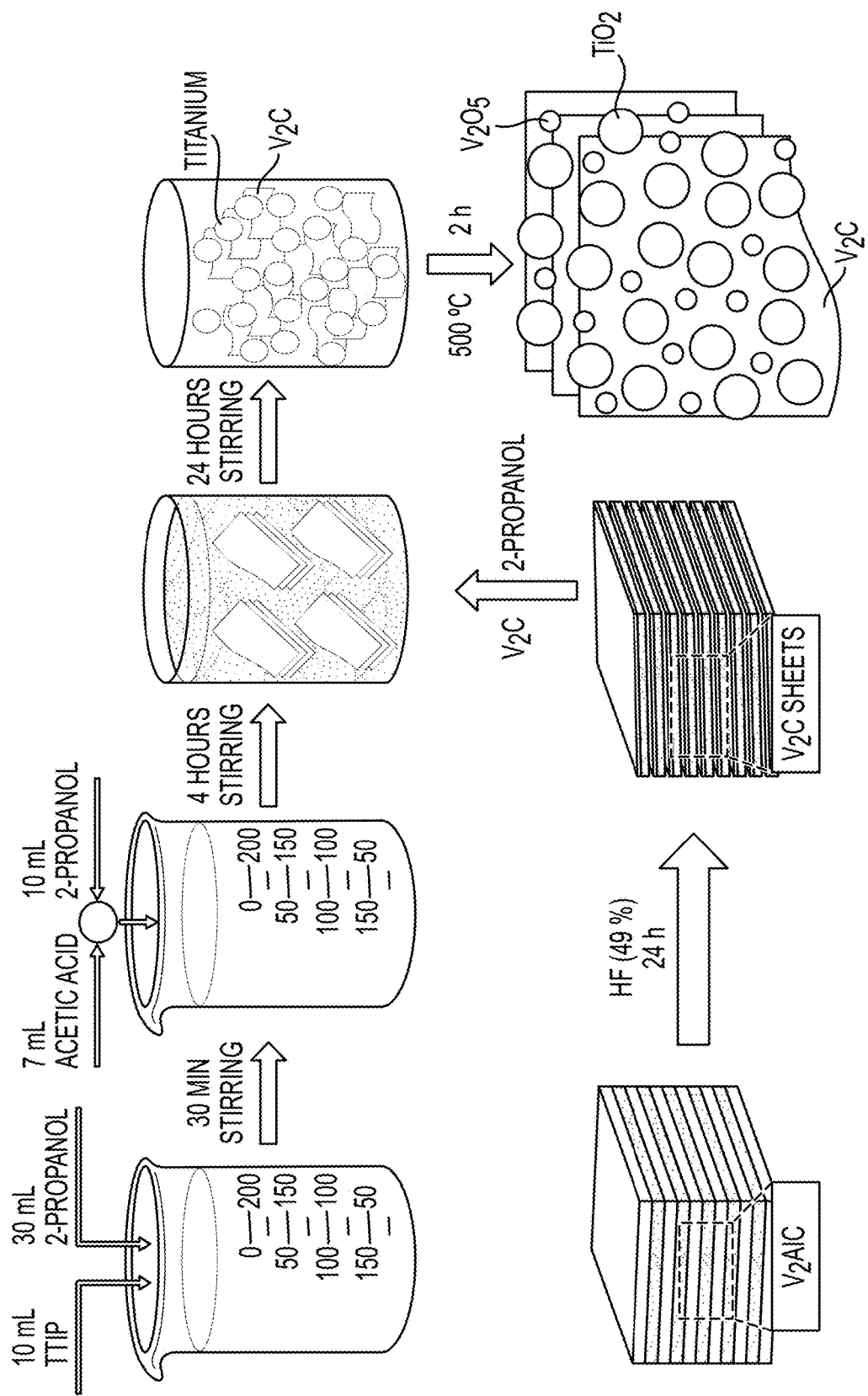
FIG. 1 shows schematic illustration for the synthesis of $V_2C$ MXene and $V_2C@V_2O_5/TiO_2$ composites.

Subsequently, the obtained product was finely ground into a fine powder and subjected to calcination for 2 hours at 500° C. The resulting material was designated as the $V_2C@V_2O_5/TiO_2$ composite with in-situ grown $V_2O_5$ and was given name $V_2C@V_2O_5/TiO_2$. To synthesize pure $TiO_2$ nanoparticles (NPs), same procedure was involved, excluding the addition of $V_2C$. The rest of the process, including the hydrolysis of TTIP, incorporation into 2-propanol, stirring, oven drying, grinding, and calcination at 500° C. for 2 hours, was maintained. This parallel process resulted in the production of pure $TiO_2$ NPs. FIG. 1 shows schematic illustration for the synthesis of $V_2C$ MXene and $V_2C@V_2O_5/TiO_2$ composites.

Characterization:

Various analytical techniques were employed to comprehensively characterize each catalyst sample. X-ray powder diffraction (XRD) analysis was conducted with the assistance of a Bruker Advance D8 diffractometer (Rigaku Smart Lab-Cu—K, $\lambda=0.154178$ nm) to examine the purity and crystal phase structures. The structural and morphological features of both the pure and composite materials were scrutinized using Scanning Electron Microscopy (SEM) on a JEOL 6010 PLUS/LA instrument. X-ray photoelectron spectroscopy (XPS), facilitated by an Axis ultra-DLD Shimadzu, was utilized to determine the elemental states. The binding energy of C is at 284.60 eV was used as a reference to calibrate all the elements high-resolution peaks. Photoluminescence (PL) spectroscopy, employing a 325 nm-wavelength laser from HORIBA Scientific, was employed to assess the materials. Additionally, a Raman analysis was conducted with a HORIBA Scientific Spectrophotometer equipped with a 532 nm laser in order to determine the interplay among the composite components. Using a Carry 100 Agilent UV-vis spectrophotometer (model #G9821A), the powder samples were safely put into a sample holder prior to analysis in order to get the UV-visible diffuse reflectance absorbance spectra.

The electrochemical impedance spectroscopy (EIS) experimentation was conducted utilizing a conventional three-electrode cell and a CS350 electrochemical workstation obtained from Wuhan Corrtest Instruments Corp., Ltd. (Wuhan, China). This widely adopted electrochemical technique provides valuable insights into the electrical properties and behavior of materials in various environments. A 0.2 M $Na_2SO_4$ solution served as the electrolyte, an Ag/AgCl electrode was used as the reference electrode, and a Pt mesh (CE) as the counter electrode. A specific amount of catalyst was dispersed in methanol, resulting in the creation of a homogeneous and dense slurry. This uniform and thick slurry was then precisely applied to the FTO (fluorine-doped tin oxide) glass, serving as the designated working electrode. The application process ensured an even coating across the entire surface of the FTO glass, emphasizing the importance of consistency and uniformity in the preparation of the working electrode for its intended applications. The coated FTO glass was allowed to dry at 80° C. before being utilized as the electrode in the electrochemical studies.

Example 3: Photocatalytic Activity Test

The photocatalytic system consists of a central reactor chamber, lamps with integrated cooling fans, mass flow controllers (MFC), and an online product analysis system. Acting as the primary light source, a 200 W Hg lamp is employed, providing a light intensity of 100 mW/cm$^2$. This lamp is strategically positioned above a quartz glass window, enabling the transmission of light into the reactor chamber. To carry either moisture or a methanol-water mixture along with $CO_2$, a water saturator is integrated into the reactor system. The experiments were conducted using 150 mg of powder catalyst which was evenly distributed on the bottom surface of the reactor. The feed mixture entered from the top, flowing over the catalyst surface before exiting at the bottom. The reactor chamber bottom surface, where the catalyst, reactants, and light source interact, was the main exposed area. Prior to commencing experiments, a feed mixture of $CO_2$ and $H_2O$ was continuously passed through the reactor for 30 minutes to saturate the catalyst surface. In the case of photocatalytic $CO_2$ reforming of methanol, a 10% methanol-water solution was prepared. $CO_2$ was then passed through the methanol solution to carry vapors of methanol-water before entering the reactor. The examination of reaction products was conducted through gas chromatography, employing Thermal Conductivity Detector (TCD) and Flame Ionization Detector (FID) systems. These detectors were linked to Carboxen-1010 PLOT capillary columns to enable the precise identification of compounds such as carbon monoxide (CO), carbon dioxide ($CO_2$), methane ($CH_4$), and hydrogen ($H_2$).

Results and Discussion

Materials Characterization

Figure 2:
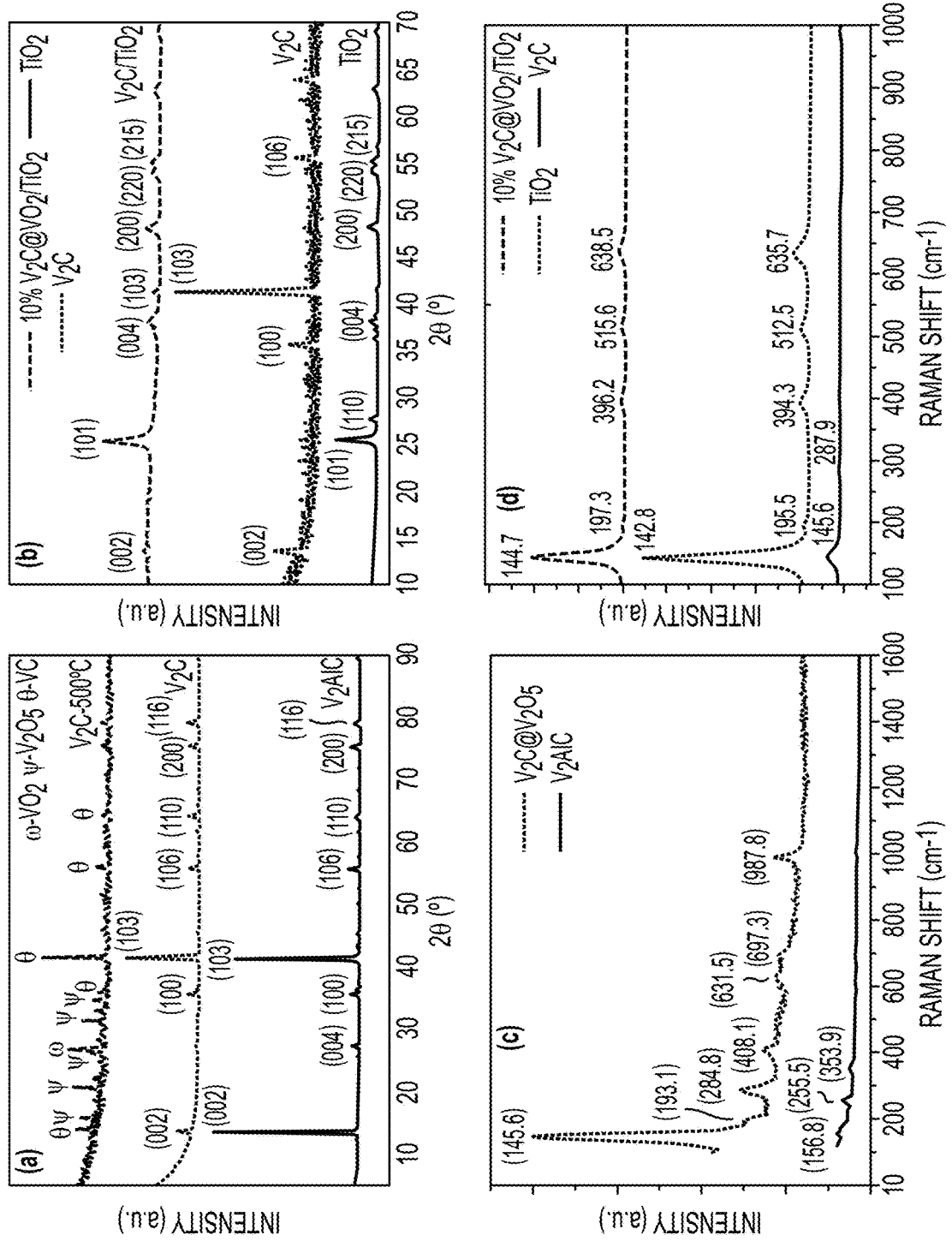
FIG. 2 shows (a) X-ray diffraction (XRD) patterns of $V_2AlC$, $V_2C$ and $V_2C$-500, (b) XRD patterns of $TiO_2$ and $V_2C@V_2O_5/TiO_2$ composite, (c-d) Raman spectra of $V_2AlC$, $V_2C$, $TiO_2$ and $V_2C@V_2O_5/TiO_2$ composites.

The crystal structures of the original $V_2AlC$ MAX, $V_2C$-MXene, and $V_2C$-500 were analyzed using X-ray diffraction (XRD) as shown in FIG. 2 (a). The 2θ peaks for the $V_2AlC$ MAX are appeared at 13.39, 35.51, 41.22, 55.55, 63.84, 75.07, and 79.93°, which are belonged to lattice plans of (002), (100), (103), (106), (110), (109), and (116), linked to $V_2AlC$ MAX. The two obvious peaks of $V_2AlC$ with lattice plans of (002) and (103) corresponding to JCPDS No. 29-0101. The peaks of $V_2C$ MXenes are located at 2θ of 13.6°, 35.7°, 41.4°, 55.7°, 64.0°, 75.3°, and 79.1° and could be indexed to lattice plans of (002), (100), (103), (106), (110), (200), and (116), corresponding to the existence of $V_2C$ MXene (JCPDS No. 29-0101). The intensity of main peak (002) of $V_2AlC$ MAX was reduced after HF etching, which confirms successful fabrication of $V_2C$ MXene after removal of Al layer. When $V_2C$ was oxidized at 500° C. for 2 hours under air atmosphere, new peaks were appeared at 2θ of 15.74, 20.52, 26.47, 31.26, and 34.600, corresponding to the existence of $V_2O_5$ (JCPDS no. 41-1426).

FIG. 2 (b) shows XRD peaks of $TiO_2$ and $V_2C$ MXene based composited. The XRD patterns of pure $TiO_2$ shows diffraction peaks belongs to lattice plans of (101), (004), (200), (220), and (215) corresponds to anatase phase of $TiO_2$. However, another lattice plan at (110) confirms the presence of rutile phase of $TiO_2$, with a lower quantity. In the case of $V_2C$ MXene/$TiO_2$ composite, XRD patterns of both the $V_2C$ and $TiO_2$ were observed. By observing the XRD pattern of $V_2C$-MXeneTiO$_2$ nanocomposite, successful fabrication was achieved using a facile sol-gel method. However, the existence of $V_2O_5$ was not observed due to lower amount of $V_2C$ loading and smaller amount of in-situ grown $V_2O_5$ nanoparticles.

Raman spectroscopy analysis was used to study phase and structural transitions of $V_2AlC$, $V_2C$, $TiO_2$ and $V_2C@V_2O_5/TiO_2$ composite samples. In FIG. 2 (c), the Raman spectra of $V_2AlC$ and $V_2C$ MXenes following the HF-etching process are depicted. In the Raman spectra of $V_2AlC$, the presence of a peak at 156.8 cm$^{-1}$ is attributed to the in-plane bond of V—Al ($E_{2g}$) within the $V_2AlC$ MAX phase. The other two peaks 255.5 and 353.9 cm$^{-1}$ are related to V-V bonds. In the case of Raman spectra of $V_2C$ MXene, several distinct peaks were appeared. The broad peak at 145.6 cm$^{-1}$ can be linked to the formation of V-C and $V_2O_5$. The $V_2AlC$ MAX peak was disappeared in $V_2C$ MXene due to exfoliation process and new peaks appeared at 284.8 and 408.1 cm$^{-1}$, which describes effective removal of Al-layer and the successful fabrication of layered MXene structure. Additionally, the emergence of a new broad peak at 284.8 cm$^{-1}$ ($E_{1g}$) further substantiates an increased distance between the layers of $V_2C$ MXene, providing confirmation of the in-plane vibration of V-atoms. Moreover, the presence of other distinct peaks at 408.1, 631.5, and 697.3 cm$^{-1}$ serves as confirmation of the effective vibrational states of terminal groups (—OH, —F, and —O) distributed across the surface of the MXene. Another obvious Raman shift peak at 987.8 cm$^{-1}$ can be assigned to the existence of $V_2O_5$ over the $V_2C$ MXene surface. In FIG. 2 (d), the Raman spectra of $TiO_2$ and $V_2C@V_2O_5/TiO_2$ composite samples are presented. The Raman spectra of pure $TiO_2$ exhibit distinct peaks at 142.8, 195.5, 394.3, 512.5, and 635.7 cm$^{-1}$, which are attributed to the anatase phase of $TiO_2$. However, when $V_2C$ was added to $TiO_2$, all the peaks were shifted to higher values. The new peaks for the $V_2C@V_2O_5/TiO_2$ composite were 144.7, 197.3, 396.2, 515.6 and 638.5 cm$^{-1}$. The shift in peaks confirm good interaction between the $V_2C$ and $TiO_2$ materials.

Figure 3:
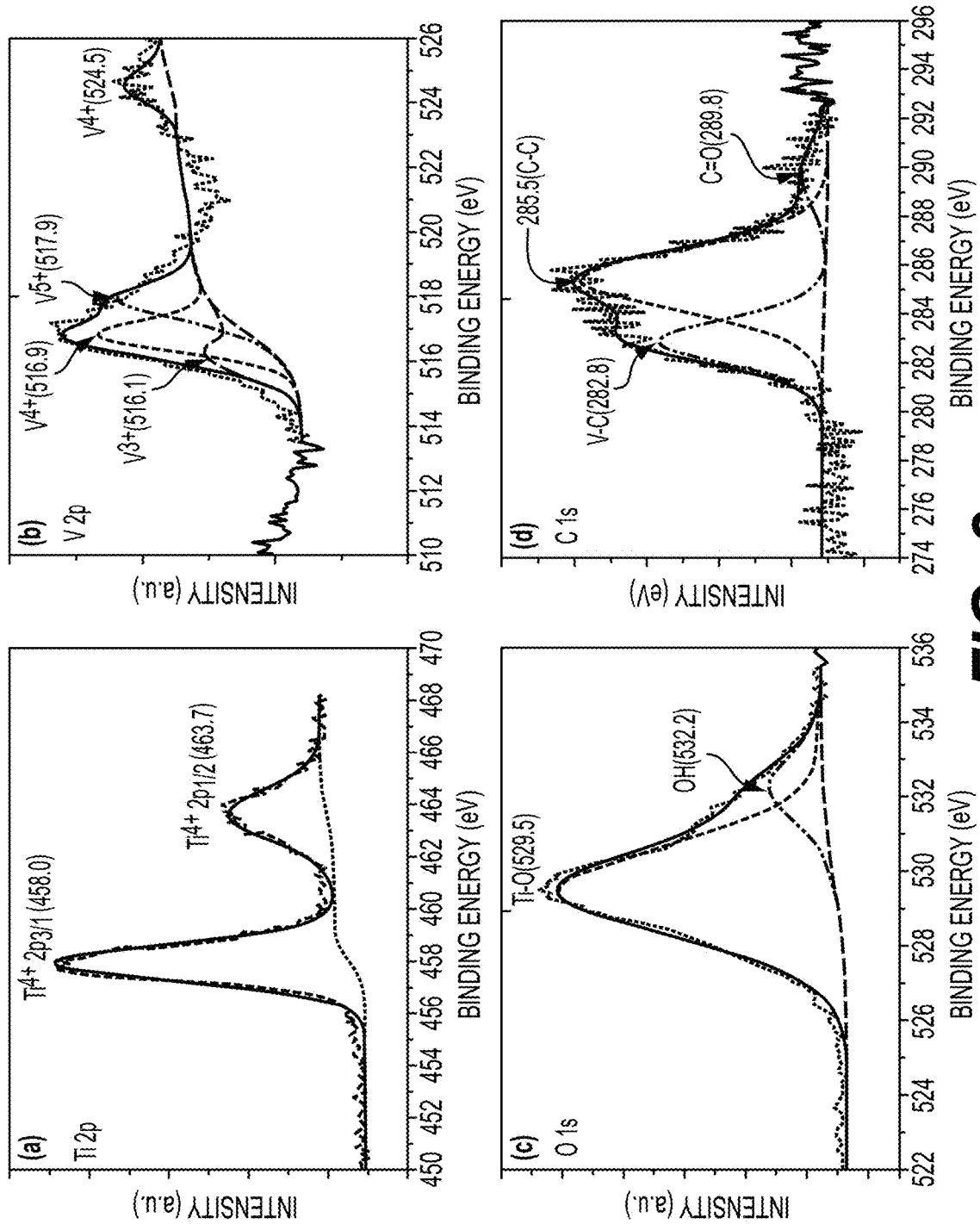
FIG. 3 shows X-ray Photoelectron Spectroscopy (XPS) analysis of $V_2C@V_2O_5/TiO_2$ composite: (a) Ti 2p, (b) V 2p, (c) O 1s, and (d) C 1s.

The surface chemical composition of $V_2C@V_2O_5/TiO_2$ was scrutinized through X-ray photoelectron spectroscopy (XPS) analysis, and the outcomes of this examination are presented in FIG. 3. This analytical approach allowed for a comprehensive exploration of the elemental composition and chemical states present on the surface of the $V_2C@V_2O_5/TiO_2$ composite material. FIG. 3 (a) shows XPS spectrum of Ti 2p with binding energies 458.8 and 463.7 eV, associated with $Ti^2p_{3/2}$ and $Ti^2p_{1/2}$, which confirms the existence of $Ti^{4+}$ in $V_2C@V_2O_5/TiO_2$. FIG. 3 (b) shows XPS spectrum of V 2p with characteristics peaks linked to $V^{3+}$, $V^{4+}$, and $V^{5+}$. The $V^{4+}$ species in $V_2C$ is associated with 516.9 and 425.5 eV, which confirm the existence of vanadium oxide (V-O) on the surface of $V_2C$. The binding energies at 516.1 and 517.9 eV are associated with $V^{3+}$ and $V^{5+}$, respectively. The XPS spectrum of O 1s have two peaks with binding energies 529.5 and 532.2 eV, which are associated to Ti—O and —OH groups, respectively. FIG. 3 (d) shows the XPS spectrum of C 1s in $V_2C@V_2O_5/TiO_2$ composite with binding energies 282.8, 285.5, 289.8 eV The principal peak at 282.8 eV in the C—V spectrum is attributable to $V_2C$, while the presence of adventitious carbon (C—C) is indicated by the peak at 285.5 eV Furthermore, the peak observed at 289.8 eV corresponds to O—C=O and is indicative of functional groups on the surface of MXene and adsorbed species present on the material surface[27]. The XPS results contribute valuable insights into the nature of the interactions between the $V_2C$ and $TiO_2$ components, shedding light on the surface chemistry and providing essential information for understanding the material properties and potential applications in photocatalytic $CO_2$ reduction.

Figure 4:
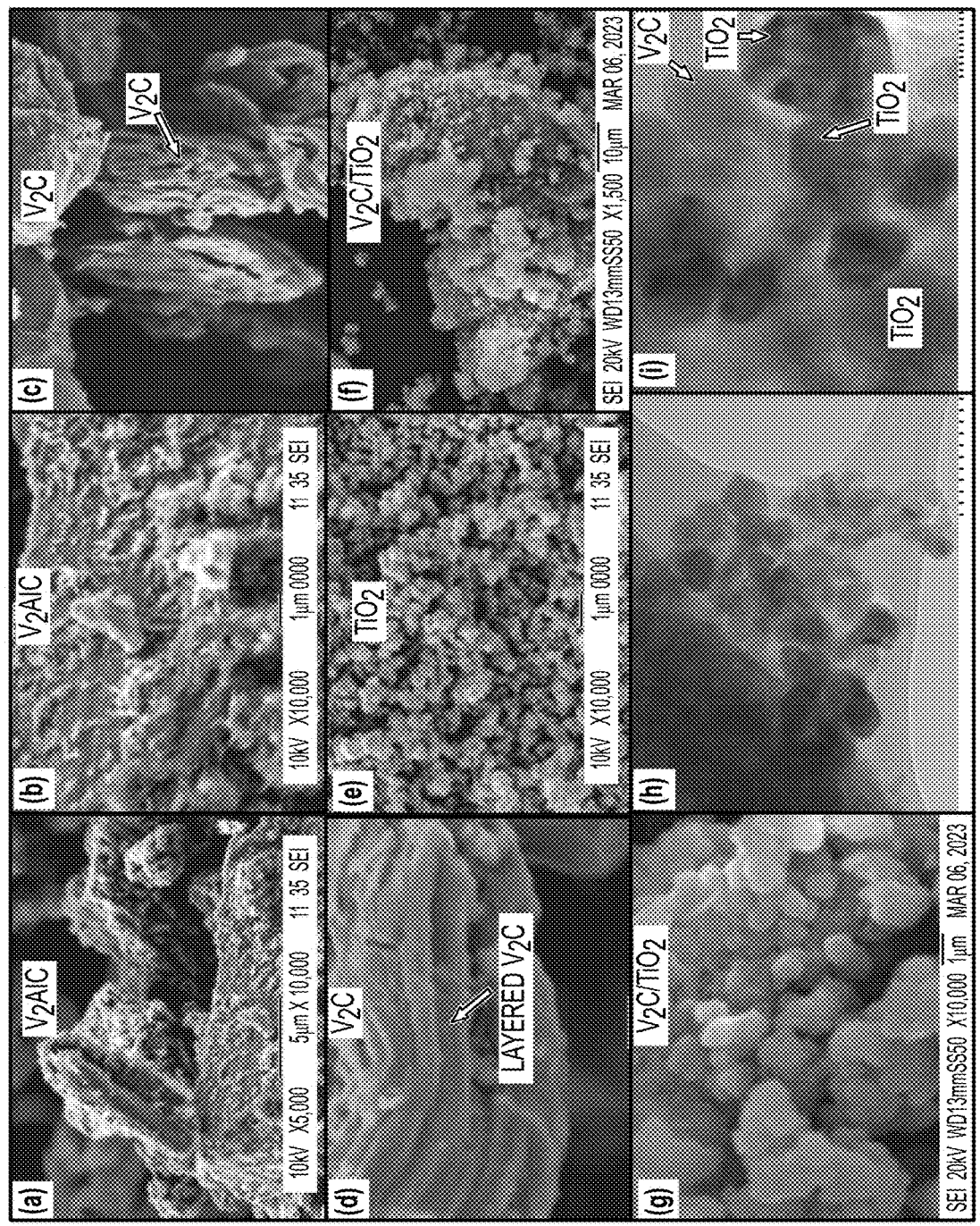
FIG. 4 shows Field emission scanning electron microscopy (FESEM) images of (a-b) $V_2AlC$ MAX phase, (c-d) $V_2C$ MXenes etched with 49% HF for 24 h, (e) $TiO_2$ anatase phase, (f-g) dispersion of $TiO_2$ NPs over $V_2C$ layered structure; TEM images of $V_2C@V_2O_5/TiO_2$ composite.

To verify the success of the chemical etching and stacking of the structure, field emission microscopy (SEM) was used to evaluate the microstructural properties of $V_2AlC$ MAX, $V_2C$ MXene, $TiO_2$, and $V_2C@V_2O_5/TiO_2$ composite. FIG. 4 (a-b) shows bulk phase of $V_2AlC$ in which all the layered are stacked together without any interlayer distance. After HF etching of $V_2AlC$ MAX, $V_2C$ MXene with obvious distance between the layers was observed. The $TiO_2$ particle of uniform size can be observed in FIG. 4 (f). When $V_2C$ MXene was added to $TiO_2$ through sol-gel method, a good interface interaction was achieved as shown in FIG. 4 (f). The high-resolution images depicted in FIG. 4 (g) serve to affirm that $TiO_2$ particles are thoroughly and uniformly dispersed across the $V_2C$ sheets, establishing a well-distributed and cohesive interface interaction.

Figure 5:
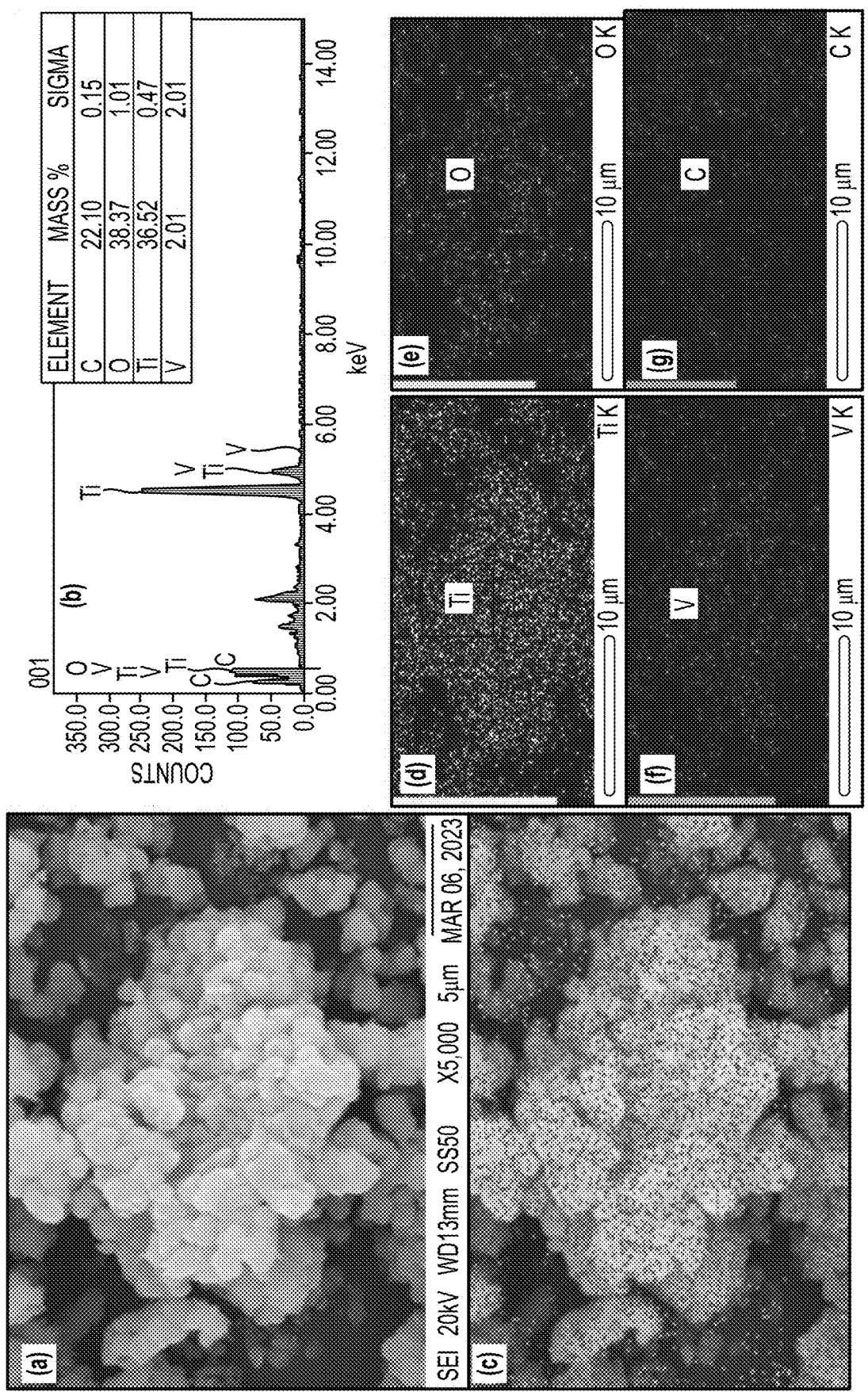
FIG. 5 shows an Energy-Dispersive X-Ray (EDX) and MAP analysis of $V_2C@V_2O_5/TiO_2$ composite: (a) SEM image of $V_2C@V_2O_5/TiO_2$, (b) EDS spectra with the existence of C, Ti, O and V elements, (c) MAP analysis of the composite, (d-g) Color images showing uniform distribution of Ti, O, V and C, respectively.

The interface interaction was further studied by transmission electron microscopy (TEM), and the outcomes are presented in FIG. 4 (h-i). The TEM images provide visual evidence of the dispersion of $TiO_2$ on the 2D $V_2C$ surface, underscoring the presence of a robust interface interaction between the two materials. FIG. 5 presents an energy-dispersive X-ray (EDX) mapping analysis of the $V_2C@V_2O_5/TiO_2$ composite. In FIG. 5(a), SEM images clearly illustrate the presence of $TiO_2$ and $V_2C$, a confirmation corroborated by the element mapping (MAP) of the constituent elements. The EDS analysis (FIG. 5b) reaffirms the existence of carbon (C), oxygen (O), titanium (Ti), and vanadium (V), with their respective compositions clearly identified. The MAP image in FIG. 5(c) exhibits a uniform distribution of all these elements across the composite material. Further insights into the distribution of specific elements are provided in FIG. 5(d-g), where individual mapping images confirm the homogeneous presence of titanium (Ti), oxygen (O), vanadium (V), and carbon (C) throughout the $V_2C@V_2O_5/TiO_2$ composite. This comprehensive EDX mapping analysis not only validates the uniform distribution of elements within the composite but also underscores the successful integration of $TiO_2$ with $V_2C$, crucial for the desired properties and performance in potential applications.

Figure 6:
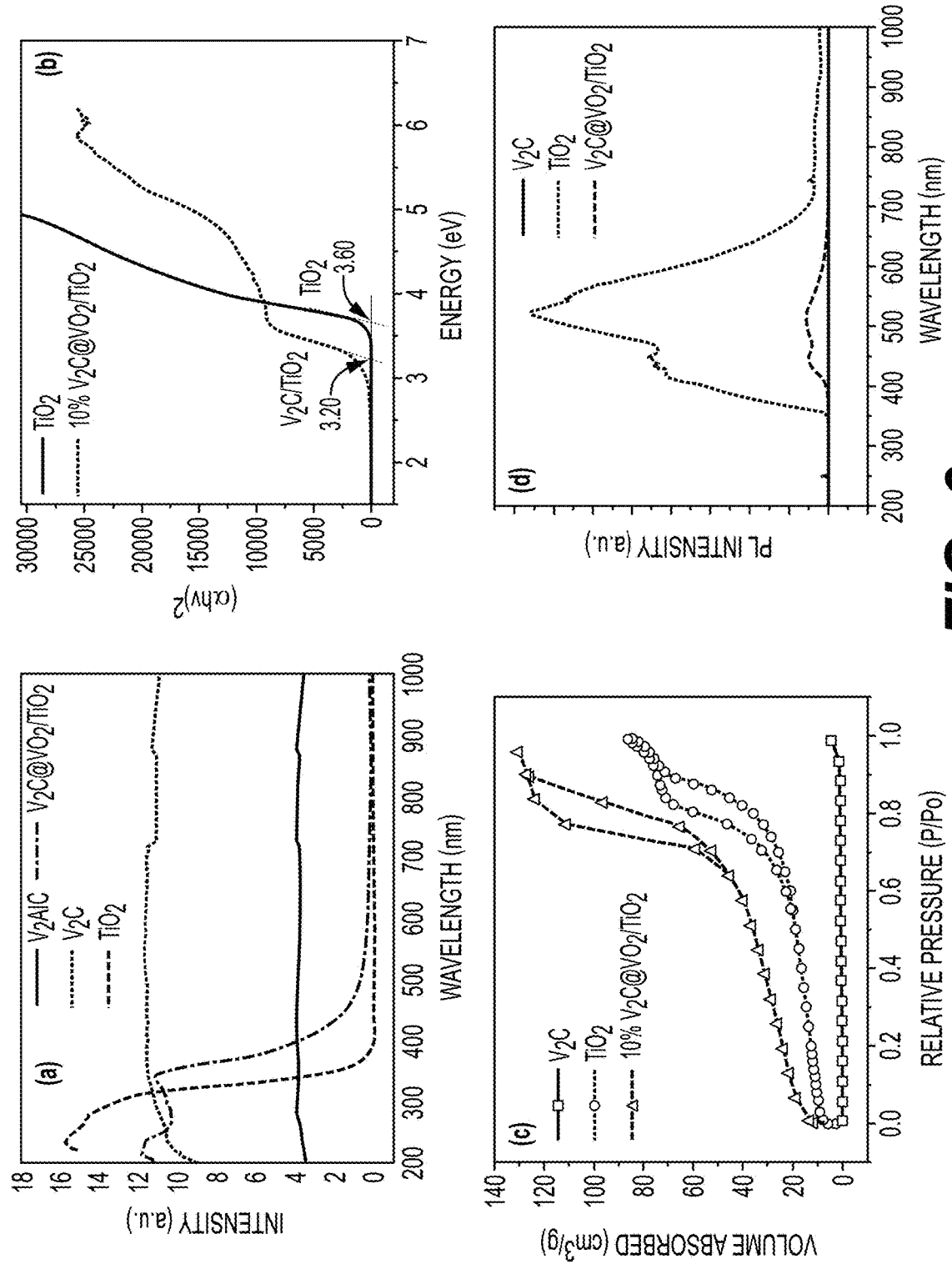
FIG. 6 shows (a) UV-vis absorption spectra of $V_2AlC$, $V_2C$, $TiO_2$ and their composites, (b) Tauc plots for band gap energy calculation, (c) $N_2$ adsorption-desorption isotherms of $V_2C$, $TiO_2$ and $V_2C@V_2O_5/TiO_2$ composite samples, (d) PL analysis of $V_2C$, $TiO_2$ and $V_2C@V_2O_5/TiO_2$ photocatalysts.

UV-visible analysis was conducted to gain additional insights into the visible light absorption capabilities of $V_2AlC$, $V_2C$, $TiO_2$ and $V_2C@V_2O_5/TiO_2$ composites and the results are shown in FIG. 6(a). Comparatively, $V_2C$ MXene has higher visible light absorption compared to $V_2AlC$ MAX due to its containing only V and C elements compared to MAX with V, Al, and C. Al-element is non-conductive and it does not have light absorbance capacity. The absorbance band edge of $TiO_2$ was in the UV-region which was shifted to visible region by $V_2C$ loading, corresponding to absorption band edge of 380 and 440 nm, respectively. Thus, introducing $V_2C$ to $TiO_2$ to construct $V_2C@V_2O_5/TiO_2$ composite enhances visible light absorption. This red shift in band edge was due to higher visible light absorbance of $V_2C$ MXene. FIG. 6(b) displays the UV-visible spectra for the $TiO_2$ and $V_2C@V_2O_5/TiO_2$ composite. The band gap energy was determined using the Tauc plot and the results are shown in FIG. 6 (b). The band gap energies were determined to be 3.60 eV for $TiO_2$ and 3.20 eV for the $V_2C@V_2O_5/TiO_2$ composites. Notably, the incorporation of $V_2C$ had a substantial impact on reducing the band gap energy of $TiO_2$. This reduction can be attributed to the dark color and heightened visible light absorbance properties of $V_2C$. These results collectively highlight that the introduction of $V_2C$ enhances the ability of $TiO_2$ to absorb visible light effectively. The significant decrease in band gap energy is particularly advantageous for photocatalytic applications, as it indicates an expanded absorption range into the visible light spectrum. The dark color and increased light absorbance of $V_2C$ contribute to the modification of the electronic structure of the composite, allowing for enhanced utilization of visible light for catalytic processes.

Nitrogen adsorption-desorption isotherms were used to calculate the BET surface areas and pore volume of $V_2C$, $TiO_2$ and $V_2C@V_2O_5/TiO_2$ composite and the results. FIG. 6 (c) shows $N_2$ adsorption-desorption isotherms of $TiO_2$, $V_2C$ and $V_2C@V_2O_5/TiO_2$ photocatalysts. In $TiO_2$ and $V_2C@V_2O_5/TiO_2$ samples, Type IV isotherms are observed due to mesoporous structure. In the case of $V_2C$, hysteresis formation is not obvious but it is relatively at high pressure, which also belongs to mesoporous structure and type IV. The surface areas and pore volumes of all the samples are summarized in Table 1. Using pure $V_2C$, very small BET surface area (0.47 m²/g) and pore volume (0.0067 cm³/g) were obtained. For the $TiO_2$ and $V_2C@V_2O_5/TiO_2$ samples, BET surface areas of 43.01 m²/g and 46.50 m²/g, respectively, were obtained. The increased in BET surface area of $V_2C@V_2O_5/TiO_2$ composite was due to controlled synthesis of $TiO_2$ with $V_2C$ MXene. Furthermore, BJH surface area of $TiO_2$ (30.93 m²/g) was increased to 77.18 m²/g due to controlled growth of $TiO_2$ NPs due to the presence of $V_2C$ using sol-gel method. Similar trends were observed in the case of pore volume, wherein the pore volume of $TiO_2$ increased from 0.0595 to 0.2018 cm³/g. This suggests that the controlled synthesis of MXene with a more porous structure resulted in a higher pore volume. Additionally, the BET surface area of $V_2C@V_2O_5/TiO_2$ increased, attributed to the controlled growth of $TiO_2$ nanoparticles facilitated by the presence of $V_2C$ MXene. This indicates that the incorporation of $V_2C$ influenced the growth and structure of $TiO_2$, leading to an augmentation in both surface area and pore volume. These results underscore the role of $V_2C$ in influencing the morphological and textural properties of the composite, providing valuable insights for applications where specific surface characteristics are crucial, such as in catalysis or adsorption processes.

Photoluminescence (PL) analysis was used to further explore the production and separation of the charges for the $V_2C$, $TiO_2$ and $V_2C@V_2O_5/TiO_2$ composite and the results are shown in FIG. 6 (d). The utilization of $TiO_2$ resulted in the highest PL intensity, suggesting an increased occurrence of charge carrier recombination within the $TiO_2$ structure. Notably, the PL intensity of pure $V_2C$ closely resembled that of a straight line due to its conductive characteristics. However, a noticeable decrease in PL intensity was observed when $V_2C$ was combined with $TiO_2$ to form the $V_2C$ MXene/$TiO_2$ composite. This reduction in PL intensity suggests a modulation in the recombination dynamics of charge carriers in the composite material. The combination of $V_2C$ with $TiO_2$ influences the charge transport and recombination processes, underscoring the impact of the composite structure on the photophysical properties, which is significant for applications in optoelectronics and photocatalysis.

Therefore, the combination of a higher BET surface area, increased pore volume, lower charge recombination rates, and improved light usage efficiency collectively contribute to the potential enhancement of photocatalytic $CO_2$ reduction. These features signify a favorable environment for catalytic processes, facilitating efficient surface interactions, improved mass transport, and reduced charge carrier recombination, which are key factors influencing the overall effectiveness of photocatalysis. The synergy of these characteristics in the composite material suggests promising applications in the domain of $CO_2$ reduction, where efficient utilization of light energy is crucial for driving catalytic reactions and converting carbon dioxide into valuable products.

TABLE 1

Surface properties of $V_2C$, $TiO_2$, and $V_2C@V_2O_5/TiO_2$ composite samples

| Samples | BET surface area (m²/g) | BJH surface area (m²/g) | Pore volume (cm³/g) | Mean pore radius (nm) |
|---|---|---|---|---|
| $V_2C$ | 0.47 | 0.78 | 0.0067 | 1.58 |
| $TiO_2$ | 43.01 | 30.93 | 0.0595 | 4.10 |
| $V_2C@V_2O_5/TiO_2$ | 46.50 | 77.18 | 0.2018 | 5.37 |

Figure 7:
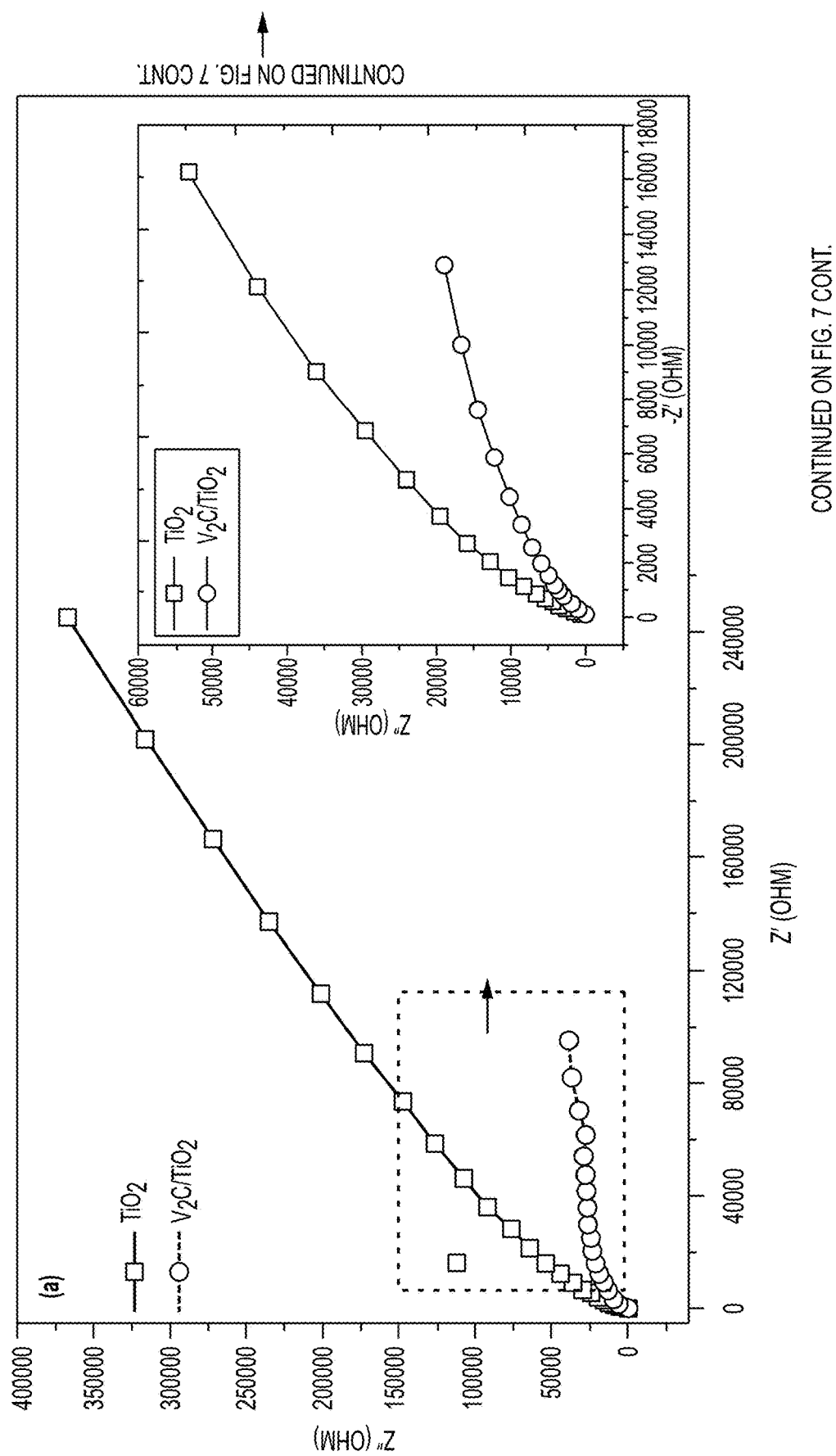
FIG. 7 shows (a) EIS analysis of $TiO_2$ and $V_2C@V_2O_5/TiO_2$ composite, (b-d) CV curves of $TiO_2$, $V_2C@V_2O_5/TiO_2$ samples.
Figure 7:
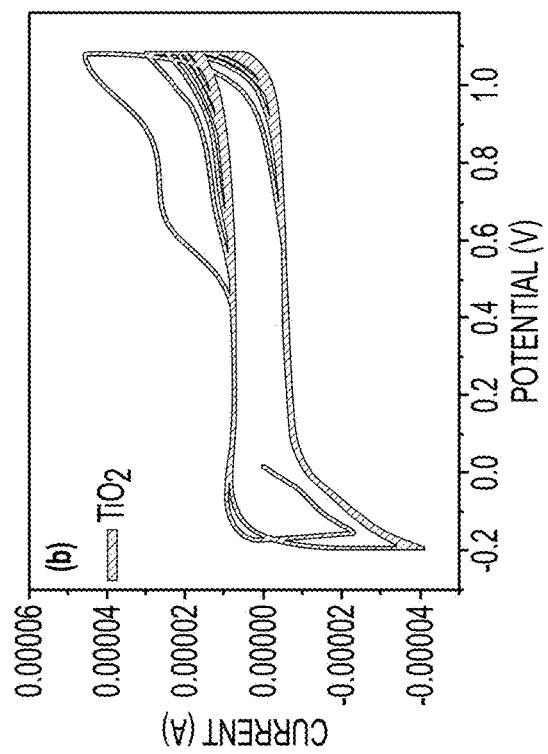
Figure 7:
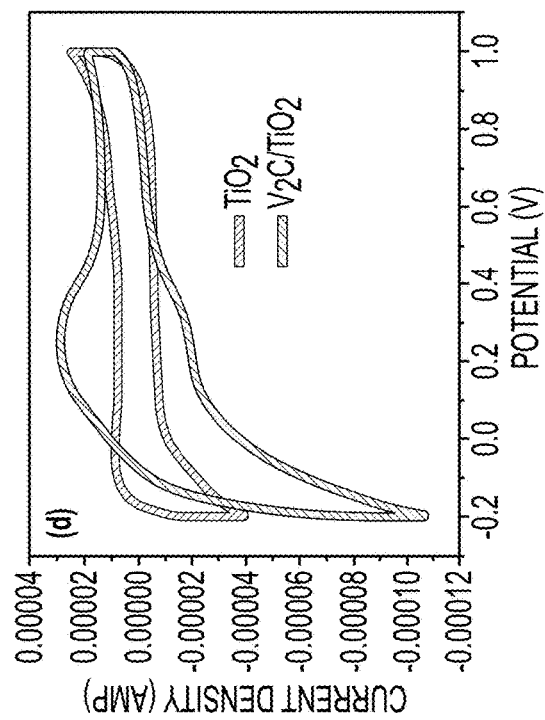
Figure 7:
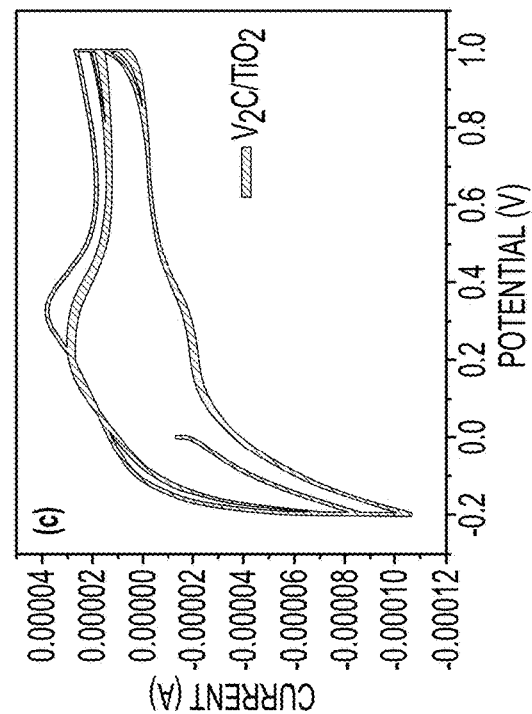

The electrochemical impedance spectroscopy (EIS) analysis of $TiO_2$ and $V_2C@V_2O_5/TiO_2$ composite is presented in FIG. 7 (a). The EIS curves for $TiO_2$ reveal a higher diameter, which is indicative of increased impedance. This higher impedance is associated with a greater recombination of charge carriers within the $TiO_2$ material. Recombination refers to the process in which separated charges (electrons and holes) recombine, leading to a reduction in the overall electrical conductivity of the material.

The introduction of $V_2C$ into the $TiO_2$ matrix has a notable impact on the EIS curves. The EIS curve for the $V_2C@V_2O_5/TiO_2$ composite exhibits a lower diameter compared to pure $TiO_2$. This reduction in diameter indicates a lower impedance for the composite material. The improved electrochemical performance is attributed to the efficient transfer of current within the $V_2C@V_2O_5/TiO_2$ composite, leading to a decrease in the recombination of charge carriers. The enhanced charge transfer efficiency in the $V_2C@V_2O_5/TiO_2$ composite can be attributed to the unique properties of $V_2C$, which may include improved conductivity, enhanced electron transport, or optimized interfaces for charge transfer. The lower impedance observed in the EIS curve signifies that the $V_2C@V_2O_5/TiO_2$ composite is better equipped to facilitate the movement of charges, resulting in improved electrochemical behavior. Thus, the introduction of $V_2C$ into the $TiO_2$ structure leads to a lower EIS curve, indicating improved charge transfer efficiency and reduced recombination.

Cyclic voltammetry (CV) is a powerful electrochemical technique that involves sweeping the potential applied to a working electrode and measuring the resulting current. This method is particularly useful for assessing the stability and reversibility of electrochemical reactions over successive cycles. The CV curves depicted in FIG. 6 (b-c) offer a comprehensive insight into the electrochemical performance of both $TiO_2$ and the $V_2C@V_2O_5/TiO_2$ composite. The overlapping nature of the CV curves for both $TiO_2$ and $V_2C@V_2O_5/TiO_2$ samples in subsequent cycles is a noteworthy observation. The fact that the curves coincide indicates that these materials exhibit excellent electrochemical stability. The CV curves of the composite overlap to a greater extent in subsequent cycles. This enhanced overlap is indicative of superior long-term cyclic stability for the $V_2C@V_2O_5/TiO_2$ composite. This enhancement may be attributed to various factors, such as increased conductivity, improved structural integrity, or optimized charge transfer kinetics. Thus, the superior overlapping of CV curves in consecutive cycles for the $V_2C@V_2O_5/TiO_2$ composite provides compelling evidence for its enhanced long-term cyclic stability compared to $TiO_2$ alone, suggesting promising prospects for practical applications.

Photocatalytic $CO_2$ Reduction

Initially, blank tests were conducted using all the photocatalysts in the process of reducing $CO_2$ with water and methanol. During these blank experiments, which involved the absence of light, $CO_2$, and photocatalyst, no additional products were detected in the gas phase. These findings reinforce the purity of the photocatalysts and affirm that the generation of products only occurred when $CO_2$ was actively reduced in the presence of light and photocatalyst. The absence of products in the blank experiments eliminates the possibility of contamination or interference, underscoring the reliability of the observed outcomes and confirming that the observed reactions were indeed driven by the photocatalysts.

Figure 8:
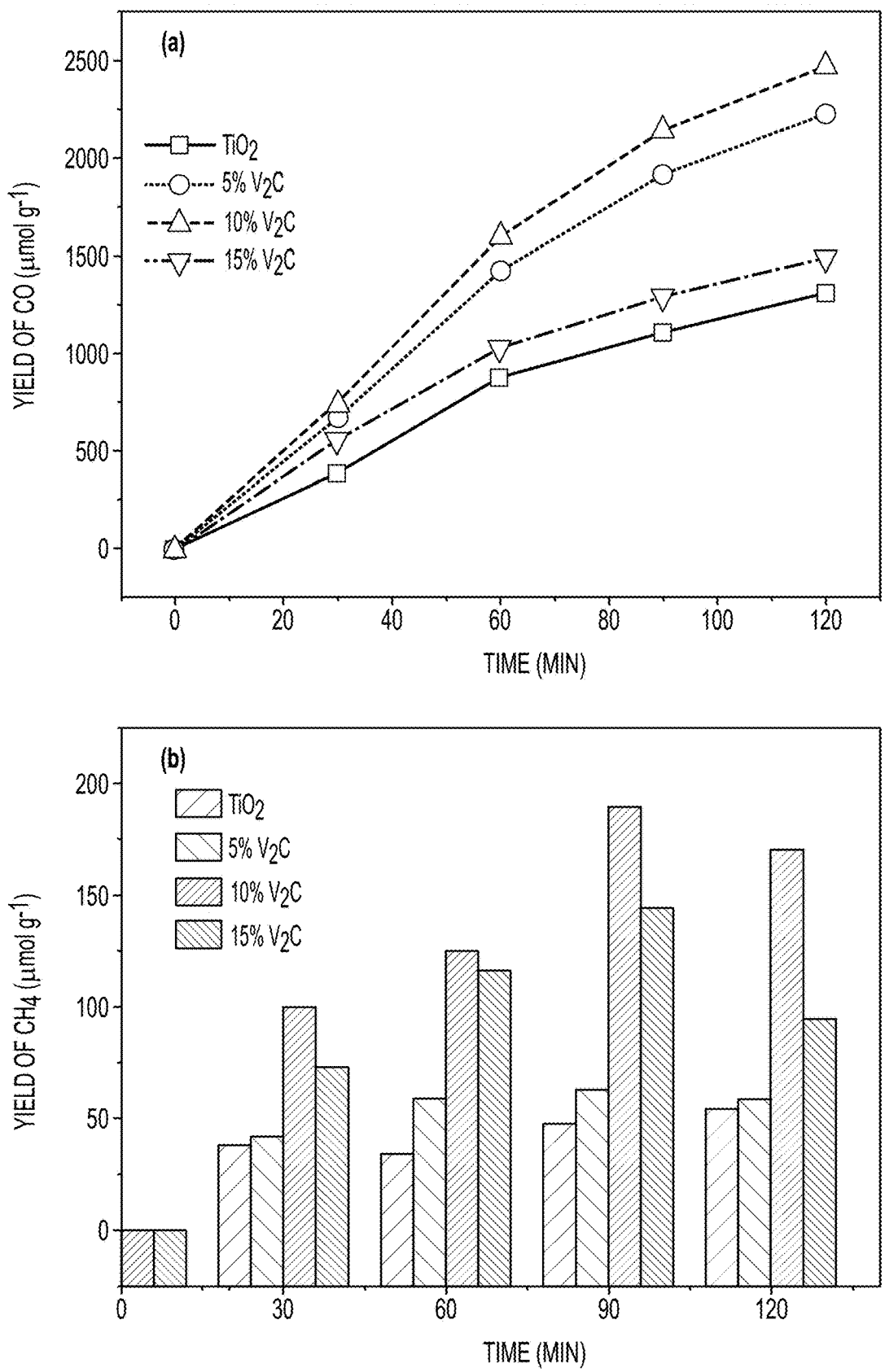
FIG. 8 shows (a) Photocatalytic $CO_2$ reduction with $H_2O$ over $V_2C@V_2O_5/TiO_2$ with various $V_2C$ loading for CO formation, (b) Photocatalytic $CH_4$ formation over $V_2C@V_2O_5/TiO_2$ with various $V_2C$ loading.

FIG. 8 illustrates the photocatalytic process of reducing $CO_2$ with $H_2O$ to generate CO and $CH_4$ in a gas phase photocatalytic system. As shown in FIG. 8 (a), CO was the primary product of photocatalytic reduction of $CO_2$ with $H_2O$. Because of charges recombining over its surface throughout the irradiation period, pure $TiO_2$ produced lower CO yield. Obviously, the photocatalytic activity of $TiO_2$ was increased when $V_2C$ was added to construct $V_2C@V_2O_5/TiO_2$ composite. The highest CO production was obtained with 10% $V_2C@V_2O_5/TiO_2$ composite, with a 2467.67 μmol/g after two hours of irradiation time, which corresponded to 1.11, 1.66 and 1.90 folds more than pure 5% $V_2C$, 15% $V_2C$ and pure $TiO_2$ samples, respectively. This provides information about the importance of $V_2C$ MXene during $CO_2$ reduction reaction under the influence of the photocatalyst ($V_2C@V_2O_5/TiO_2$), providing valuable insights into the efficiency and selectivity of the photocatalytic system for producing CO and $CH_4$ as desired products.

Photocatalytic $CO_2$ reduction to $CH_4$ over $TiO_2$ and $V_2C$-loaded $TiO_2$ photocatalysts is demonstrated in FIG. 8 (b). The highest $CH_4$ production was obtained with 10% $V_2C@V_2O_5/TiO_2$ loadings but in a small amount compared to CO formation. The decrease in CO formation with higher $V_2C$ loading can be linked to charge recombination centers and more surface coverage by $V_2C$, resulting in lower photocatalytic efficiency. Well-designed $V_2C@V_2O_5/TiO_2$ structure helps to increase the light utilization and expose multiple catalytic active sites. Besides, synergistic effect of $V_2C/V_2O_5$ with $TiO_2$ enhances charge separation efficiency. The $V_2C$ MXene sheets serves as a conductive material that facilitates and promotes efficient electron transport. All of these characteristics support the notion that the well-designed ($V_2C@V_2O_5/TiO_2$) may be regarded as a potential non-noble photocatalyst for photocatalytic $CO_2$ reduction applications.

The performance of $V_2C@V_2O_5/TiO_2$ was further investigated using various reforming systems such as $CO_2$ reduction with $H_2O$, $H_2$ and methanol. In order to investigate the role of methanol as a hole scavenger, $CO_2$ gas was first saturated with methanol-water vapors using a 5 vol. % solution of methanol in water. FIGS. 9 (a-b) depict the performance of $V_2C@V_2O_5/TiO_2$ in the photocatalytic reduction of $CO_2$ to CO under various reaction systems. Using water and $H_2$, lower amount of CO was produced. In the case of $CO_2$ reduction with $H_2$, initially, higher amount of CO was produced but its production was not continuous with irradiation time. These results showcase the effectiveness of the $V_2C@V_2O_5/TiO_2$ composite in facilitating the conversion of carbon dioxide into carbon monoxide through photocatalytic processes. However, continuous CO generation was seen using water and methanol feed mixtures. Comparatively, using $CO_2$ reduction with $H_2O$ and $H_2$, lower amount of CO was produced, which was significantly enhanced with methanol as the sacrificial reagent. The methanol-water mixture exhibited the highest CO yield, reaching a maximum of 40150 µmol $g^{-1}$. This value is notably 16 times greater compared to the utilization of $CO_2$ with water and $H_2$. The superior performance of the methanol-water mixture highlights its effectiveness as a reaction system for enhancing the photocatalytic reduction of $CO_2$ to CO using the $V_2C@V_2O_5/TiO_2$ composite. This shows that reducing $CO_2$ to create CO over $V_2C@V_2O_5/TiO_2$ using methanol as a sacrificial reagent is a promising strategy. This was clearly caused by increased proton and electron production during the photocatalysis process, which reduced $CO_2$ to form CO.

The production of $CH_4$ during photocatalytic $CO_2$ reduction with $H_2O$ and $H_2$ is presented in FIG. 9 (c). Using $CO_2$ reduction with $H_2$, highest $CH_4$ formation of 359 µmol $g^{-1}$ was obtained, which is 2.1 times more than it was produced using only water. This higher amount of $CH_4$ formation was possibly due to activation of $CO_2$ methanation reaction, which is a favorable process in most of the $CO_2$ reduction reactions. The performance of $V_2C@V_2O_5/TiO_2$ composite was further tested using methanol as the sacrificial reagent and the results of $CH_4$ formations are presented in FIG. 9 (d). The yield of $CH_4$ generated was lower with $H_2O$ and $H_2$ feed mixtures, but it was much boosted with the use of a methanol-water mixture. With a methanol-water mixture, the maximum $CH_4$ generation of 35133 µmol $g^{-1}$ was achieved, 97.8 times greater than with $H_2$ and 206.7 folds higher than using only water. This reaffirms methanol as a promising sacrificial reagent for the production of CO and $CH_4$ in the $CO_2$ reduction process. The observed results underscore the efficacy of methanol in facilitating enhanced photocatalytic activity and product yields in the $CO_2$ reduction reaction, making it a notable candidate for sacrificial reagent applications.

These findings were subjected to further evaluation based on the selective formation of CO and $CH_4$ within the $CO_2$—$H_2O$, $CO_2$—$H_2$, and $CO_2$—$CH_3OH$—$H_2O$ reaction systems. The outcomes of this evaluation are depicted in FIG. 9 (e-f). FIG. 9 (e) specifically illustrates the production of CO and $CH_4$ over $V_2C@V_2O_5/TiO_2$ during the $CO_2$ reduction process with $H_2O$. Obviously, CO was obtained as the main product which was 14.5 folds higher than $CH_4$ formation after 2 hours of irradiation time. This shows $V_2C@V_2O_5/TiO_2$ is selective for CO formation when $CO_2$ was reduced with water only. On the other hand, when $CO_2$ was reduced with methanol-water mixture, CO and $CH_4$ were produced in a significant amount as shown in FIG. 9 (f). However, the production of CO was 1.14 folds higher than $CH_4$ formation, which further confirms higher efficiency of $V_2C@V_2O_5/TiO_2$ composite for the formation of both CO and $CH_4$. Most importantly, an $H_2$ yield of 1456.9 µmol $g^{-1}$ was obtained when $CH_3OH$—$H_2O$ was used instead of only water. These findings support that methanol is a suitable reducing agent for initiating $CO_2$ reduction by methanol reforming, which produces a sizable amount of CO and $CH_4$ in addition to hydrogen.

It is evident from the preceding discussion that photocatalytic $CO_2$ reduction over $V_2C@V_2O_5/TiO_2$ was more important for the formation of CO and $CH_4$ when methanol was used as the reducing agent in addition to hydrogen evolution. When $CO_2$ reduction was carried out via bi-reforming of methanol with $CH_3OH/H_2O$ feed mixture, yields of CO and $CH_4$ were markedly enhanced, which can be explained through different philosophies. The $V_2C@V_2O_5/TiO_2$ composite would adsorb methanol more successfully, facilitating to increase the quantity of protons ($H^+$), which could enhance the $CO_2$ reduction reaction. Using methanol as the sacrificial agent in our previous study on photocatalytic water splitting, it was observed a significant generation of $H_2$ and $CH_4$. The researchers previously investigated the effectiveness of $Ti_3C_2$ loaded g-$C_3N_4$ with in-situ grown $TiO_2$ and tested for photocatalytic $CO_2$ reduction in the presence of several reducing agents, including water, $H_2$, and $CH_3OH$. It was demonstrated that feed mixtures containing $CO_2$ and $H_2O$ are effective for producing CO, while methanol aided in the production of more $CH_4$. Recently, $TiO_2/Bi_2MoO_6$ composite was tested for photocatalytic $CO_2$ reduction with the highest CO yield of 183.97 µmol/g within 6 h of irradiation time. The formation of S-scheme heterojunction, which facilitates the separation and transfer of photogenerated charge carriers was responsible of the increased photocatalytic activity.

The present work exhibits superiority over the previously published work in the literature as it not only produced a large amount of CO but also produces $CH_4$ and $H_2$. Higher photocatalytic efficiency for $CO_2$ reduction to usable products was the consequence of the synergistic impact of functional groups and vanadium atoms produced over $V_2C$, enabling efficient separation of photoinduced charges. All these findings collectively demonstrate that $V_2C$ can be employed directly as a cocatalyst in conjunction with other semiconductors for renewable energy applications, showcasing its versatility beyond its conventional use solely for energy storage purposes. This suggests the potential of $V_2C$ in contributing to various aspects of renewable energy and photocatalysis.

The performance of $V_2AlC$ MAX and $V_2C$ MXene was further investigated by coupling with $TiO_2$ NPs and they were tested for photocatalytic $CO_2$ reduction with the formation of CO, $CH_4$ and $H_2$. FIG. 10 (a) displays the results of CO formation during initial testing of $V_2AlC$ MAX/$TiO_2$ and $V_2C$ MXene/$TiO_2$. Continuous CO production was obtained during the entire irradiation time in both the composite samples. While MXene nanotexture produced a stable state after two hours of irradiation, MAX structure produced CO with variation in trends. The observed discrepancy in reaction kinetics, most likely stemming from the inherently slower kinetics of the MAX structure compared to the more conductive nanotexture of $V_2C$ MXene, played a pivotal role in the experimental outcomes. After two hours of irradiation, the $V_2C@V_2O_5/TiO_2$ composite exhibited the highest CO yield, reaching 40150 µmol $g^{-1}$. Importantly, this yield was 1.46 times greater than that obtained with the $V_2AlC/TiO_2$ composite. The larger BET surface area and higher conductive characteristics of $V_2C$ MXene with better charge transfer separation during the photocatalysis process were the causes of this appreciable increase in $CO_2$ reduction efficiency for CO evolution with $V_2C$ MXene.

In FIG. 10 (b), the photocatalytic $CO_2$ reduction to $CH_4$ is illustrated over $V_2AlC$ MAX/$TiO_2$ and $V_2C$ MXene/$TiO_2$ composite samples. Notably, employing $V_2C@V_2O_5/TiO_2$ resulted in a $CH_4$ production of 35133 µmol g$^{-1}$, a striking 52.8 times higher than that achieved with the $V_2AlC/TiO_2$ composite. This substantial increase in $CH_4$ production over $V_2C@V_2O_5/TiO_2$ is attributed to the fact that $CH_4$ requires 8 electrons, in contrast to the 2 electrons needed for CO formation during the $CO_2$ reduction process. The enhanced production of $CH_4$ over $V_2C@V_2O_5/TiO_2$ is attributed to its superior conductivity, enabling efficient transmission of electrons for $CO_2$ reduction and facilitating the separation of charge carriers. Similarly, the production of $H_2$ reached 1456.87 µmol g$^{-1}$ over $V_2C@V_2O_5/TiO_2$, marking a 1.35-fold increase compared to $V_2AlC/TiO_2$ (FIG. 10 (c)). This underscores the promise of $V_2C@V_2O_5/TiO_2$ for the simultaneous production of CO, $CH_4$, and $H_2$ during $CO_2$ reforming of methanol, highlighting its efficacy in charge carrier production and separation.

FIG. 10 (d) further consolidates these observations by comparing the electrical conductivity of $V_2C$ and $V_2AlC$. The significantly higher electrical conductivity of $V_2C$ plays a pivotal role in efficiently trapping electrons from $TiO_2$ and facilitating their separation. These results collectively emphasize the potential of $V_2C@V_2O_5/TiO_2$ as a more efficient photocatalyst for $CO_2$ reduction processes, showcasing its superiority in charge carrier management and product yield compared to $V_2AlC/TiO_2$.

A schematic representation of charge separation over MAX and MXene nanotextures is presented in FIG. 10 (e-f). Due to its less conductive properties, the MAX phase has a poorer charge separation efficiency than MXene, as was previously discussed. Additionally, MAX bulk structure has light absorption compared to MXene nanosheets, which is important for photocatalysis. The bulk structure of $V_2AlC$ is depicted in FIG. 10 (e), where all of the sheets are packed together. There would be less interface interaction between $V_2AlC$ and $TiO_2$ particles because of bulky materials. More charge recombination and reduced charge transfer efficiency would therefore be feasible. In contrast, $V_2C$ has a multi-layer structure (FIG. 10(f)), which offers a high light penetration rate and good interface contact with $TiO_2$, resulting in efficient charge carrier separation.

The stability analysis of the $V_2C@V_2O_5/TiO_2$ composite for photocatalytic $CO_2$ reduction with methanol was extensively examined over four consecutive cycles. At the conclusion of each cycle, the lamp was deactivated, and feed gases were introduced to cleanse the reactor before initiating the subsequent run. In FIG. 11 (a), the performance of the $V_2C@V_2O_5/TiO_2$ composite for the successive formation of CO is illustrated over the four cycles. This investigation aimed to assess the sustained efficiency and durability of the photocatalyst across multiple cycles, providing valuable insights into its stability and robustness for prolonged use in the targeted photocatalytic process. In the first cycle of $CO_2$ reduction, a lesser yield of CO was produced; in the second cycle, this yield was increased. However, a significant increase in CO formation was achieved after four complete cycles. This could possibly be due to the oxidation of the intermediate of vanadium oxide, resulting in efficient separation of charge carriers. This could also be as a result of intermediate carbon compounds that were adsorbed over the catalyst's surface during the photocatalysis process reacting through various reforming processes and turning into CO. This demonstrates that, through the bi-reforming of methanol, $V_2C@V_2O_5/TiO_2$ composite, improved stability for CO evolution during $CO_2$ photoreduction was achieved. Prior to this, the $Ti_3C_2$ coupled g-$C_3N_4/TiO_2$ composite was evaluated for four cycles; however, after the fourth cycle, stability was somewhat decreased.

FIG. 11 (b) displays the $V_2C@V_2O_5/TiO_2$ composite stability assessment for the production of $CH_4$ during the course of four consecutive cycles. As was seen in the first cycle, highest $CH_4$ was produced, however, it was decreased in the next cycles. Similarly, as demonstrated in FIG. 11 (c), constant and consistent $H_2$ production was achieved during photocatalytic $CO_2$ reduction using methanol as the sacrificial reagent. According to all of these findings, $V_2C@V_2O_5/TiO_2$ composite is a promising material that may produce CO continuously without deactivating, even after four cycles. The performance of $V_2C/g$-$C_3N_4$ composite in a fixed bed photoreactor for photocatalytic $CO_2$ reduction using an $H_2O$/methanol combination was recently reported; however, in cyclic runs, the composite catalyst lost stability.

To understand the change the structure and crystallinity of the spent $V_2C@V_2O_5/TiO_2$ composite catalyst, it was further tested utilizing X-ray diffraction (XRD). The obtained results, as illustrated in FIG. 11 (d), indicate a similarity in peak positions between the fresh and spent catalysts. Notably, no additional peaks were observed, suggesting that the catalyst structure and composition remained unaltered throughout the $CO_2$ reduction process after consecutive four cycles. This confirms that the $V_2C$ dispersed $TiO_2$ composite was stable and it can be used for multiple runs without any change in structure and sustained potential for effective performance in $CO_2$ reduction reactions under high-intensity light radiation.

The spent catalyst was further tested through SEM and EDX analysis and the results are shown in FIG. 12. SEM image in FIG. 12 (a) shows good interface interaction even after four consecutive cycles. This shows, during $CO_2$ reduction reaction with methanol sacrificial reagent, there was no effect on altering the morphology. Similarly, as shown in FIG. 12 (b), all the elements were intact over the composite surface, however, $V_2C$ and $TiO_2$ elements were segregated from each other. This was obviously due to $V_2C$ as a 2D materials contact with 0D $TiO_2$ compound and their elements could not be uniformly mixed together. EDX analysis in FIG. 12 (c) shows the presence of V, Ti, O and C elements. All these results are in good agreement of XRD analysis of the spent $V_2C@V_2O_5/TiO_2$ composite.

Table 2 provides a comprehensive summary of the performance comparison among $TiO_2$, $V_2C@V_2O_5/TiO_2$, and $V_2AlC/TiO_2$ photocatalysts in the context of photocatalytic $CO_2$ reduction using various sacrificial reagents to produce CO, $CH_4$, and $H_2$. The results highlight the substantial influence of both the type of photocatalyst and the choice of reducing agents on yield rates and selectivity. When pure $TiO_2$ was employed with $H_2$ as the reducing agent for photocatalytic $CO_2$ reduction with $H_2O$, CO and $CH_4$ were produced at rates of 655 and 27 µmole g$^{-1}$ h$^{-1}$, respectively, with selectivity values of 96% and 4.0%, respectively. The addition of 10% $V_2C$ to $TiO_2$ enhanced its photocatalytic activity, resulting in increased CO and $CH_4$ yield rates of 1234 and 85 µmole g$^{-1}$ h$^{-1}$, with selectivity values of 93.6% and 6.4%, respectively.

When $CO_2$ reduction was carried out with a methanol-water mixture, the $V_2C@V_2O_5/TiO_2$ composite exhibited notable performance, yielding CO, $CH_4$, and $H_2$ at rates of 20075, 17567, and 728.4 µmole g$^{-1}$ h$^{-1}$, with selectivity values of 52.3%, 45.8%, and 1.90%, respectively. Methanol reduction of $CO_2$ was identified as a more promising method for producing CO and $CH_4$ compared to using hydrogen and pure water. In comparison, under the same experimental conditions, V₂AlC/TiO₂ exhibited lower efficiency, with CO, CH₄, and H₂ production rates of 13750, 333, and 538 µmole g⁻¹ h⁻¹, and selectivity values of 94.0%, 2.3%, and 3.7%, respectively. This reduced efficiency was attributed to the less conductive characteristics and compact layered structure of V₂AlC/TiO₂, leading to inefficient charge carrier separation.

The performance of the current study was additionally assessed by comparing it with the research reported in the literature. In the current work, V₂C-assisted ECN nanotexture was tested for photocatalytic CO₂ reduction with methanol as the reducing agent and carbon monoxide (CO) emerged as the primary product, demonstrating a yield rate of 9289 µmol g⁻¹ h⁻¹. This amount of CO yield was a 2.21-fold increase compared to pristine g-C₃N₄. The enhanced yield was reported due to the efficient separation of charge carriers facilitated by the conductive properties of V₂C MXene. In another study, maximum methane (CH₄) yield rate of 2103.5 µmol g⁻¹ h⁻¹ was attained with a selectivity of 96.59%, utilizing the ternary g-C₃N₄/TiO₂/Ti₃AlC₂ 2D/0D/2D composite. This achievement represents a significant enhancement due to S-scheme heterojunction, being 2.73 and 7.45 times higher compared to the use of binary g-C₃N₄/Ti₃AlC₂ MAX and TiO₂ NPs/Ti₃AlC₂ samples, respectively. The yields of CH₄ and CO achieved with C/Ag@TiO₂ were 5.46 µmol·g⁻¹·h⁻¹ and 1.51 µmol·g⁻¹·h⁻¹, respectively, with the molar ratio of CH₄ reaching the highest value at 78.3%. In another development, MIL-68 (In)-derived In₂O₃@TiO₂ was tested for photocatalytic CO₂ reduction and highest CH₄ yield of 11.1 µmol g⁻¹ h⁻¹ and selectivity 659 of 88.1%. Similarly, NH₂-MIL-101(Fe)@Ti₃C₂ QDs catalyst, optimized with 0.75 wt % Ti₃C₂ QDs, achieved a CO-evolution rate of 55.7 µmol h⁻¹ g⁻¹. This rate was 2.6 times greater than that observed with pristine NH₂-MIL-101(Fe) due to efficient charge carrier separation. To summarize, the proximity of V₂C MXene to TiO₂ facilitated efficient charge carrier separation, leading to a substantial enhancement in photocatalytic activity. The synergistic collaboration of V₂O₅ and V₂C with TiO₂ played a crucial role in this improvement, resulting in significantly higher photocatalytic efficiency for CO and CH₄ production through CO₂ reforming reaction.

TABLE 2

Summary of production rate and selectivity over various V₂C/TiO₂ based reaction systems.

| Catalyst | Reducing agent | Production rate (µmol g⁻¹ h⁻¹) | | | Selectivity (%) | | |
|---|---|---|---|---|---|---|---|
| | | CO | CH₄ | H₂ | CO | CH₄ | H₂ |
| TiO₂ | H₂O | 655 | 27.0 | 0.0 | 96.0 | 4.0 | 0.0 |
| 10% V₂C/TiO₂ | H₂O | 1234 | 85.0 | 0.0 | 93.6 | 6.4 | 0.0 |
| 10% V₂C/TiO₂ | H₂ | 1220 | 179.7 | | 87.2 | 12.8 | 0.0 |
| 10% V₂C/TiO₂ | 5% MeOH | 20075 | 17567 | 728.4 | 52.3 | 45.8 | 1.90 |
| 10% V₂AlC/TiO₂ | 5% MeOH | 13750 | 333 | 538 | 94.0 | 2.3 | 3.7 |

The photocatalytic reduction of CO₂ to CO, CH₄, and H₂ over the V₂C@V₂O₅/TiO₂ composite was further examined by considering the charge carrier separation and reduction potential of the products. The conceptual illustration of this photocatalytic CO₂ reduction process using the V₂C@V₂O₅/TiO₂ composite for the generation of CO, CH₄, and H₂ is presented in FIG. 13. It provides insights into the mechanism and pathways involved in the photocatalytic reactions, shedding light on the interactions between V₂C@V₂O₅/TiO₂ and CO₂, leading to the formation of the targeted products. The photogenerated charges under light irradiation on the TiO₂ surface can recombine due to their short lifespan. However, effective separation of photoinduced charges with minimal recombination was achieved because of the heterojunction design between V₂O₅ and TiO₂. Due to appropriate work function of V₂CT$_x$ (φ=4.5 eV), it would be useful to trap and transport electrons from TiO₂. V₂C and TiO₂ possessed the right fermi level, allowing for efficient electron transport at the interface. During photocatalysis process under light irradiation over TiO₂, holes (h⁺) and electrons (e⁻¹) are produced. The electrons were trapped to V₂C from TiO₂, resulting in their efficient separation due to difference in their work function.

During photocatalytic CO₂ reduction over TiO₂, upon light irradiation electrons and holes are produced Eq. (1). The electrons TiO₂ CB were transferred to VC, thus intriguing for trapping and transporting electrons from TiO₂ Eq. (2). The holes and water are used for the oxidation of water and methanol for the production of protons, as shown by Eq. (3) and (4). The electrons and protons were consumed for the production of CO, CH₄ and H₂ according to the reaction in Equations (5)(7), respectively.

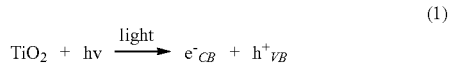
(1)

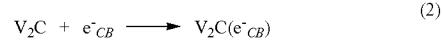
(2)

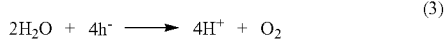
(3)

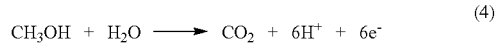
(4)

(5)

In summary, due to close interaction between the V₂C MXene and TiO₂, efficient charge carrier separation was achieved, and the photocatalytic activity was substantially improved by the synergistic action of V₂O₅ and V₂C with TiO₂.

The invention claimed is:

1. A composite photocatalyst comprising V₂C@V₂O₅/TiO₂; wherein V₂C is from about 5 to about 30 wt. %; V₂O₅ is from about 1 to about 10 wt. %; and TiO₂ is from about 60 to about 99 wt. %.

2. The composite photocatalyst of claim 1, wherein V₂C@V₂O₅/TiO₂ is a composite of V₂C@V₂O₅/TiO₂ with in-situ grown V₂O₅; and it has a two-dimensional (2D)/zero-dimensional (0D)/zero-dimensional (0D) structure.

3. The composite photocatalyst of claim 1, wherein $TiO_2$ is distributed over the whole surface of $V_2C$.

4. The composite photocatalyst of claim 1, wherein all the elements of the composite (V, C, Ti and O) are evenly distributed within the composite.

5. The composite photocatalyst of claim 1, wherein the composite photocatalyst is for $CO_2$ reduction.

6. A process for $CO_2$ reduction comprising contacting a feed comprising $CO_2$ and at least one sacrificial compound with a composite photocatalyst of claim 1; and irradiating the photocatalyst with at least one irradiation source.

7. The process of claim 6, wherein the sacrificial compound comprises water, $H_2$, methane, methanol, ethanol, acetic acid, propanol, glycerol, TEOA, or a mixture thereof.

8. The process of claim 7, wherein the process selectively produces CO when $CO_2$ reduction is carried out with water, and the process increases methane and hydrogen production by introducing methanol through dry reforming.

9. The process of claim 6, comprising:
 a) providing a photocatalytic system comprising a main reactor chamber, cooling fans integrated with an irradiation light source, mass flow controllers (MFC), and an online products analysis system;
 b) utilizing an irradiation source positioned above an optical interface which allows light/irradiation passage through the reactor system;
 c) integrating a water saturator with the reactor system for carrying the at least one sacrificial compound with $CO_2$;
 d) introducing the feed at the top of the reactor and allowing it to flow over the composite photocatalyst surface before exiting at the bottom surface; and
 e) passing the feed through the reactor before starting the experiments to saturate the catalyst surface.

10. The process of claim 6, wherein the process is carried out at room temperature and atmospheric pressure.

11. The process of claim 6, wherein the process is carried out in liquid phase and/or in gas phase.

* * * * *